(12) United States Patent
Sumi

(10) Patent No.: US 8,324,584 B2
(45) Date of Patent: Dec. 4, 2012

(54) CASSETTE TYPE RADIOGRAPHIC IMAGE SOLID-STATE DETECTOR

(75) Inventor: Makoto Sumi, Tokorozawa (JP)

(73) Assignee: Konica Minolta Medical & Graphic, Inc. (JP)

( * ) Notice: Subject to any disclaimer, the term of this patent is extended or adjusted under 35 U.S.C. 154(b) by 0 days.

(21) Appl. No.: 13/311,828

(22) Filed: Dec. 6, 2011

(65) Prior Publication Data

US 2012/0153172 A1 Jun. 21, 2012

(30) Foreign Application Priority Data

Dec. 15, 2010 (JP) .................................. 2010-278971

(51) Int. Cl.
*G01T 1/24* (2006.01)
(52) U.S. Cl. ............................... 250/370.08; 250/370.11
(58) Field of Classification Search .............. 250/361 R, 250/362, 370.08, 370.09, 370.11, 484.4
See application file for complete search history.

(56) References Cited

FOREIGN PATENT DOCUMENTS

| JP | 9-73144 A | 3/1997 |
|---|---|---|
| JP | 2002-311527 A | 10/2002 |
| JP | 2005-114944 A | 4/2005 |
| JP | 2005-121783 A | 5/2005 |

*Primary Examiner* — Mark R Gaworecki
(74) *Attorney, Agent, or Firm* — Cantor Colburn LLP

(57) ABSTRACT

A cassette type radiographic image solid-state detector includes: a detector unit having a scintillator for converting incident radiation into light and a detection section which receives and converts the light converted by the scintillator into electric signals; and a housing containing the detector unit, the housing having a rectangular tubular housing body which has openings at both ends and is formed in a rectangular tube shape using carbon fiber, and a first cover member and a second cover member for covering the openings of the rectangular tubular housing body, wherein a wall of the rectangular tubular housing body facing to a direction perpendicular to an incident direction of radiation is thicker than a wall of the rectangular tubular housing body facing to the incident direction of radiation.

10 Claims, 16 Drawing Sheets

FIG. 6a
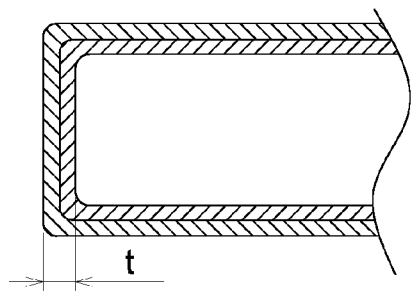
FIG. 6b
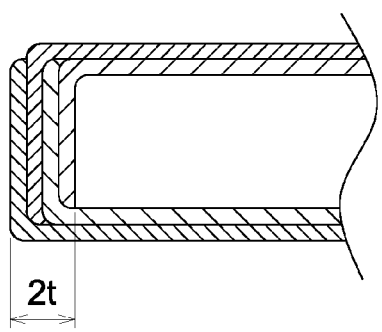
FIG. 7
|  | MODULUS OF ELASTICITY | THERMAL CONDUCTIVITY |
| --- | --- | --- |
| PAN-BASED CARBON FIBER | 230 Gpa | 0.6 - 3.1 W / mk |
| PITCH-BASED CARBON FIBER | 790 Gpa | 220 W / mk |
| ALUMINUM | 73 Gpa | 237 W / mk |
FIG. 8
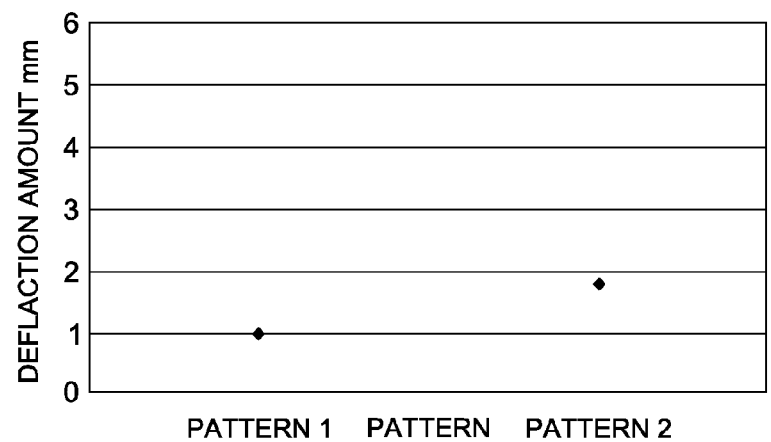

FIG. 11

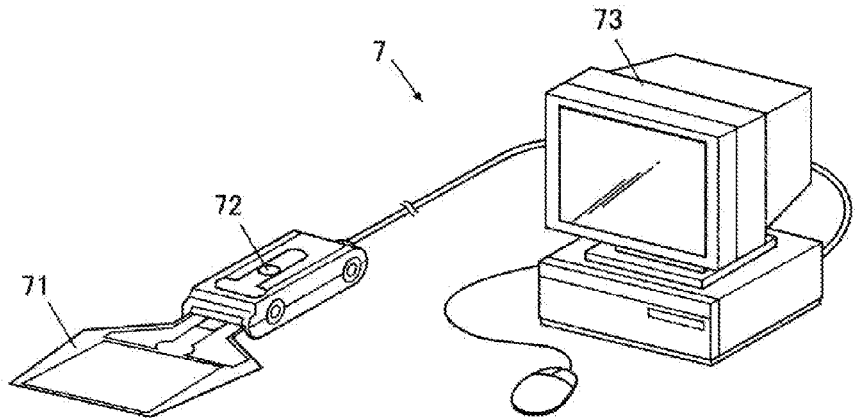

FIG. 12

UNIT: MPa(kgf/cm²)

| TYPE OF GLASS | NOMINAL THICKNESS | SHORT TERM PERMISSIBLE STRESS | | LONG TERM PERMISSIBLE STRESS | |
|---|---|---|---|---|---|
| | | IN-PLANE ($\sigma$ ae) | EDGE ($\sigma$ ae) | IN-PLANE ($\sigma$ ae) | EDGE ($\sigma$ ae) |
| FLOAT PLATE GLASS, HEAT-ABSORBING PLATE GLASS, HEAT-REFLECTING PLATE GLASS | LESS THAN OR EQUAL TO 8 mm | 24.5 (250) | 17.7 (180) | 9.8 (100) | 6.9 (70) |
| | MORE THAN 8 mm AND LESS THAN OR EQUAL TO 12 mm | 22.1 (225) | 17.7 (180) | 8.8 (90) | 6.9 (70) |
| | MORE THAN 12 mm AND LESS THAN OR EQUAL TO 20 mm | 19.6 (200) | 17.7 (180) | 7.8 (80) | 6.9 (70) |
| | MORE THAN 20 mm | 18.6 (190) | 17.7 (180) | 7.4 (75) | 6.9 (70) |
| LINED/POLISHED LINED GLASS | | 19.6 (200) | 9.8 (100) | 7.8 (80) | 3.9 (40) |
| LINED/FIGURED LINED GLASS | | 14.7 (150) | 9.8 (100) | 5.9 (60) | 39 (40) |
| HARDENED GLASS | | 88.3 (900) | 79.4 (810) | 73.5 (750) | 68.6 (700) |
| DOUBLE HARDENED GLASS | | 44.1 (450) | 35.3 (360) | 29.4 (300) | 24.5 (250) |

FIG. 13

| | IN THE CASE OF 4 SIDES SUPPORTED | NOTE |
|---|---|---|
| GLASS SIZE mm a | 364.6 | |
| GLASS SIZE mm b | 440.6 | |
| b/a | 1.2 | |
| $\beta_1$ | 0.362 | |
| $\alpha_1$ | 0.064 | |
| GLASS THICKNESS mm t | 1.2 | BEING SET AS 0.6 mm X 2 = 1.2 |
| WEIGHT ON GLASS kg | 11.1 | |
| WEIGHT ON GLASS N | 108.78 | 1kg=9.8N |
| UNIFORMLY-DISTRIBUTED WEIGHT W N/m² | 677 | |
| UNIFORMLY-DISTRIBUTED WEIGHT W MPa | 0.00067715 | |
| YOUNG'S MODULUS OF PLATE GLASS E MPa | 71600 | |
| MAXIMUM STRESS $\sigma$ MPa | 23 | |
| MAXIMUM DEFLECTION AMOUNT $\delta$ mm | 6 | |
| PERMISSIBLE STRESS MPa | 24.5 | |

COEFFICIENT VALUE: $\beta_1, \alpha_1$

| b/a | 1.0 | 1.1 | 1.2 | 1.3 | 1.4 | 1.5 | 1.6 | 1.7 | 1.8 | 1.9 | 2.0 |
|---|---|---|---|---|---|---|---|---|---|---|---|
| $\beta_1$ | 0.272 | 0.318 | 0.362 | 0.403 | 0.441 | 0.475 | 0.507 | 0.535 | 0.580 | 0.583 | 0.603 |
| $\alpha_1$ | 0.046 | 0.055 | 0.064 | 0.703 | 0.081 | 0.088 | 0.094 | 0.100 | 0.106 | 0.111 | 0.115 |

CASSETTE TYPE RADIOGRAPHIC IMAGE SOLID-STATE DETECTOR

RELATED APPLICATION

This application is based on Japanese Patent Application No. 2010-278971 filed on Dec. 15, 2010 in Japanese Patent Office, the entire content of which is hereby incorporated by reference.

TECHNOLOGY FIELD

The present invention relates to a cassette type radiographic image solid-state detector.

BACKGROUND TECHNOLOGY

Heretofore, radiation images represented by an X-ray image, which is photographed by using radiation, have been widely used for the purpose of disease diagnosis or the like.

Up to now, such radiation images for medical use had been photographed using a screen film, but in recent years, digitization of the radiation images has been realized. For example, a CR (computed radiography) apparatus has been widely used (for example, refer to Japanese Patent Application Publication Nos. 2005-121783 and 2005-114944), in which radiation which passed through an object is accumulated on a photostimulable phosphor sheet on which a photostimulable phosphor layer is formed, after which, the photostimulable phosphor sheet is scanned with a laser light, and then photostimulable light emitted from the photostimulable phosphor sheet, due to the above laser scanning, is subjected to a photoelectric conversion to obtain image data.

In photographing radiation images, there is used a cassette, in which a recording medium such as a screen film and/or a photostimulable phosphor sheet is stored inside the above cassette (for example, Japanese Patent Application Publications Nos. 2005-121783 and 2005-114944). A cassette used for CR, which is used for photographing with the CR apparatus, is designed and manufactured according to JIS standard size for a cassette used for the aforesaid screen/film so that the existing equipment, such as a cassette holder and a Bucky (wall type or table type) which were introduced to fit in with the cassette used for the conventional screen/film, can be successively used. In other words, the interchangeability of the cassette is maintained, and effective utilization of the equipment and digitization of image data have been achieved.

Further, in recent years, as a means to obtain radiation images for medical use, a FPD (flat panel detector) has been known as a detector which detects radiated radiation and obtains the radiation as digital image data (for example, refer to Japanese Patent Application Publication No. H9-73144).

Further, portable imaging equipment in which the above FPD is stored in a housing (a portable FPD) has been practically used (for example, refer to Japanese Patent Application Publication No. 2002-311527, and U.S. Pat. No. 7,189,972). Such portable detector is expected to be widely used because it is possible to carry out photographing in a sickroom or the like, since the detector is easy to carry, and further, it is possible to freely adjust the position or angle of the detector according to the position or angle of the body to be photographed.

The portable detector is structured so as to be easily carried with a handle being attached at an end of a housing which stores the FPD, as described in Japanese Patent Application Publication No. 2002-311527, and U.S. Pat. No. 7,189,972.

As it was described above, the cassette for the CR which is currently widespread is designed to have a size conformable to JIS standard size in the conventional cassette for screen/film system, and the Bucky and the like are also made conforming to the JIS standard size. Therefore, if the FPD can be used in such a form that the FPD is stored in a cassette conforming to the JIS standard size, existing equipment installed in facilities can be used for photographing using the FPD, and thereby the investment in plant and equipment, when the FPD as an photographing means is introduced, can be minimized.

However, the detector described in Japanese Patent Application Publication No. 2002-311527, and U.S. Pat. No. 7,189,972 is not conformable to the above JIS standard size, as is also clear from the fact that a handle is attached to the detector, and therefore the detector has a shape such that the detector is unable to use the existing facilities.

Further, if the detector receives an impact such as when dropped on a floor or the like, the housing is deformed, and then a glass substrate or electric parts inside the housing are overloaded, and as a result, breakage of the parts or deterioration of image quality may be caused.

On that point, in the case where a handle is attached to the housing, since the detector is carried with the handle being held, the detector is dropped with its end portion opposite to the handle facing down when the detector is dropped in error. Due to the reason, in the case where the detector is a simple portable one such as described in Japanese Patent Application Publication No. 2002-311527, and U.S. Pat. No. 7,189,972, it is only necessary to make the detector so as to withstand an impact from an expected direction of such dropping.

On the other hand, since a cassette conforming to the above JIS standard size is a thin planar one with no handle being attached, it is not specified which part of the cassette should be held when it is carried, and therefore, when it is dropped, it is impossible to predict how it will be dropped and which part of the cassette will be impacted when it is dropped. In addition, in the case of such cassette, since a degree of freedom of a cassette loading position (the loading direction) at photographing the patient also significantly increases, it is also impossible to predict that, from which direction, the weight (a load) of the patient will be added to the cassette at a time when the cassette position with respect to the patient is modified. Due to the reason, there is an issue that it is necessary to increase the overall strength of the cassette.

Therefore, the present invention was achieved to solve the above issue, and it is an object of the present invention to provide a cassette type radiation image solid-state detector which is a FPD being able to achieve digitization of image data, has sufficient strength while maintaining the amount of penetrating radiation even if the FPD is thin such that it is interchangeable with a cassette used for CR, is possible to restrain deformation of the housing against stress from the outside, and therefore, can cope with an impact from the outside, and it is possible to carry out a portable photographing including full load photographing.

SUMMARY

To achieve the above object, one aspect of the present invention is a cassette type radiographic image solid-state detector comprising: a detector unit including a scintillator for converting incident radiation into light and a detection section which receives and converts the light converted by the scintillator into electric signals; and a housing containing the detector unit, the housing including a rectangular tubular housing body which has openings at both ends and is formed in a rectangular tube shape using carbon fiber, and a first cover member and a second cover member for covering the openings of the rectangular tubular housing body, wherein a wall of the rectangular tubular housing body facing to a direction perpendicular to an incident direction of radiation is thicker than a wall of the rectangular tubular housing body facing to the incident direction of radiation.

BRIEF DESCRIPTION OF THE DRAWINGS

FIGS. 6a and 6b are drawings explaining structures of the housing body of the present embodiment and a comparative example.

FIG. 7 is a table comparing a modulus of elasticity and thermal conductivity of various materials.

FIG. 8 is a graph showing a simulation result on the deflection amount of a housing.

FIG. 11 is a drawing showing a schematic constitution of a pressure measuring apparatus.

FIG. 12 is a table explaining an allowable stress of a glass substrate.

FIG. 13 is a table explaining the maximum stress and the maximum deflection amount of a four-side support glass substrate.

FIG. 29b is an E-E sectional view of FIG. 29a.

MODE FOR CARRYING OUT THE INVENTION

Hereinafter, an embodiment of the cassette type radiographic image solid-state detector relating to the present invention will be described with reference to FIG. 1 to FIGS. 24a to 24c. However, the scope of the invention is not limited to the illustrated examples.

Figure 1:
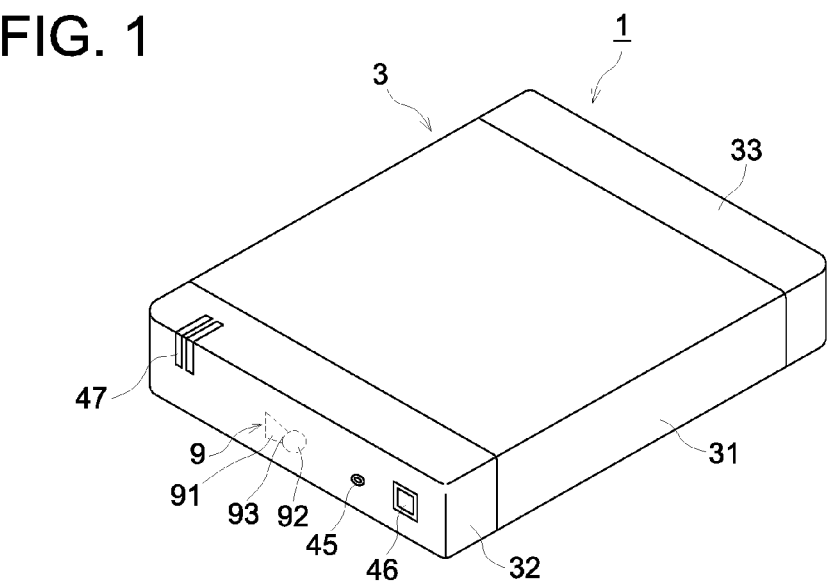
FIG. 1 is a perspective view showing the cassette type detector relating to the present embodiment.

FIG. 1 is a perspective view showing the cassette type radiographic image solid-state detector relating to the present embodiment (hereinafter, it is referred to as a "cassette type detector").

Cassette type detector 1 in the present embodiment is a cassette type flat panel detector (hereinafter, it is referred to as a "FPD"), and cassette type detector 1 is provided with detector unit 2 (refer to FIG. 16 and the like) which detects radiated radiation and obtains the radiation as digital image data, and housing 3 which stores above detector unit 2 in the inside of housing 3.

Figure 2:
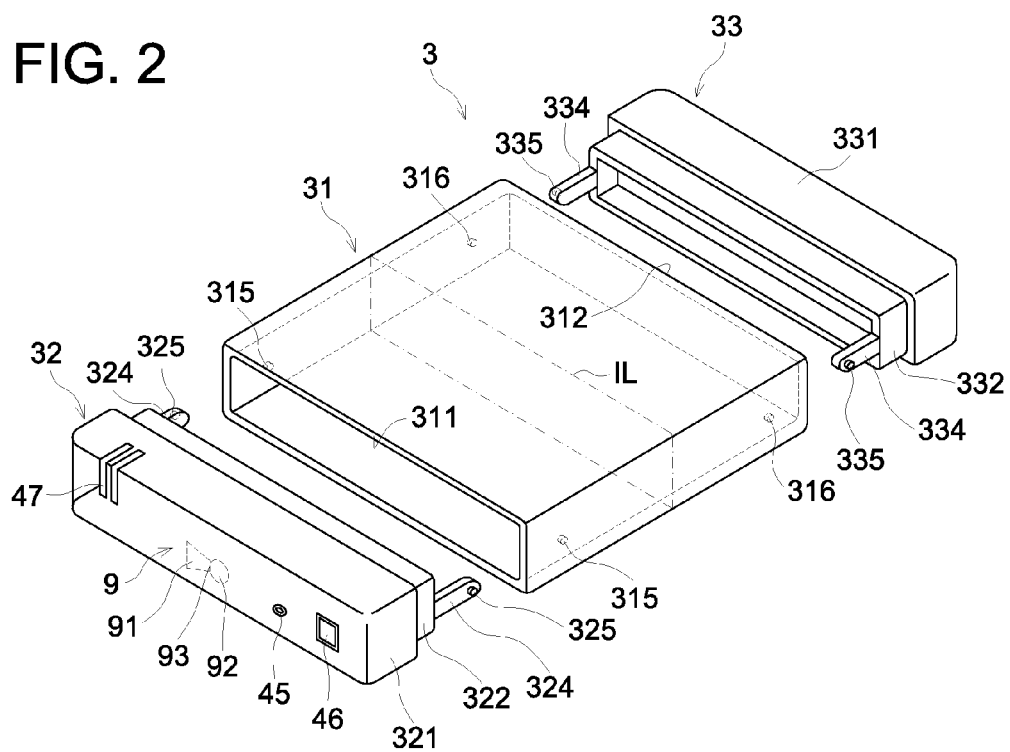
FIG. 2 is a broken perspective view of a housing in the present embodiment.

FIG. 2 is a broken perspective view of a housing in the present embodiment.

As it is shown in FIG. 2, housing 3 is provided with housing body 31 which is formed in a hollow rectangular tube shape having openings 311 and 312 at the both ends, and first cover member 32 and second cover member 33 which cover and block each of openings 311 and 312 of housing body 31.

In the present embodiment, housing 3 is formed so that the thickness of the wall of the housing body 31 facing to the incident direction of radiation becomes 15 mm. The thickness of the wall of the housing body 31 facing to the incident direction of radiation of housing 3 is not limited to 15 mm, but it is preferably less than or equal to 16 mm, and is preferably a size within a range of size (15 mm+1 mm and 15 mm−2 mm) conforming to JIS standard (JIS Z 4905) for a cassette used for the conventional screen/film system. The international standard corresponding to the JIS standard (JIS Z 4905) is IEC 60406.

Since most of the existing apparatuses such as a cassette used for the CR and a Bucky are made to conform to JIS standard size for a cassette used for the screen/film system, existing facilities can be utilized even in a case where photographing is carried out using cassette type detector 1, which is a cassette type FPD by adjusting the size of housing 3 to the JIS standard size.

First cover member 32 and second cover member 33 are provided with cover bodies 321 and 331 and insertion sections 322 and 332, and are formed by, for example, a non-electrically conductive material such as a non-electrically conductive plastic.

Cover bodies 321 and 331 is formed in such a manner that circumference thereof is nearly equal to the circumference of each of openings 311 and 312 of housing body 31. Further, the size of cover bodies 321 and 331 in the insertion direction with respect to openings 311 and 312 is 8 mm. Though how much is the above size of cover bodies 321 and 331 should be designed is not particularly limited, but regarding cover body 321 in which antenna device 9 to be described later is arranged, the above size is preferably more than or equal to 6 mm, and is further preferable if it is more than or equal to 8 mm.

Further, insertion sections 322 and 332 are in a frame shape having an opening at the insertion side with respect to openings 311 and 312, and are formed in such a manner that the circumference of insertion sections 322 and 332 becomes a little smaller than the internal circumference of each of openings 311 and 312 of housing body 31.

In the inside of insertion sections 322 and 332, there are arranged buffer members 323 and 333 (refer to FIG. 16 or the like) which can relieve an external force transferred from outside of detector unit 2. Buffer members 323 and 333 are not particularly limited as long as it can relieve an external force, and, for example, foamed urethane, silicon, and the like can be applied.

In particular, the cross-section shape of buffer member 333, which is arranged at insertion section 332, is in nearly a "V" shape (refer to FIGS. 18 and 24), and the member may be formed of any one of an elastic body, a viscous body and a viscoelastic body, and is preferably a member which is deformable when detector unit 2 is brought into close contact with the member. Buffer members 323 and 333 also function as a holding member which holds detector unit 2 at an adequate position in the inside of housing 3.

From each side of insertion sections 322 and 332, engagement pieces 324 and 334, as an engaging means which engages housing body 31 with cover members 32 and 33, extend toward the insertion direction with respect to openings 311 and 312. At each of outer side surfaces of engagement pieces 324 and 334, engaging convex parts 325 and 335 are arranged.

At each of outer peripheries of insertion sections 322 and 332, a waterproof ring (not illustrated) is preferably arranged. In the case where the waterproof ring is arranged, housing body 31 adheres more tightly with each of cover members 32 and 33, and thereby it becomes possible to prevent dust, sweat of patience, water from an antiseptic solution or the like, or foreign matter from entering into the inside of housing 3.

At the surface which is a side surface of cover body 321 of first cover member and intersects at right angles with radiation entering surface of cassette type detector 1, antenna device 9 to transmit and receive information by air between cassette type detector 1 and outside equipment is embedded.

Antenna device 9 is provided with electric supply section 93 which connects a pair of metal-made planar radiation plates 91 and 92 with a pair of radiation plates 91 and 92, and supplies electricity to the aforesaid pair of radiation plates 91 and 92.

In the present embodiment, of the pair of radiation plates 91 and 92, one radiation plate 91 is formed so that the shape viewed from the front is trapezoid, and the other radiation plate 92 is formed so that the shape viewed from the front is nearly circular. Electric supply section 93 is connected with nearly the center of the upper bottom part of one radiation plate 91, and at the same time is connected with a part of the other radiation plate 92.

The connection by electric supply section 93 forms a prescribed gap between a pair of radiation plates 91 and 92.

The type and shape of antenna device 9 is not limited to those exemplified here. Further, antenna device 9 is not limited to the case of being embedded in cover body 321, and may be pasted to the outside or inside of cover body 321. Since antenna device 9 decreases receiving sensitivity and reception gain if it is arranged at a position near the electrically conductive member composed of an electrically conductive material such as metal and carbon, antenna device 9 is preferably arranged at a position away as much as possible from housing body 31 which is formed of electrically conductive material such as carbon or various electronic components 22 (refer to FIG. 16 or the like), and antenna device 9 is preferably away by at least 6 mm, and more preferably more than or equal to 8 mm.

Regarding this point, as it was described above, antenna device 9 is arranged at cover body 321 formed of non-electrically conductive material, and the size of cover body 321 in the insertion direction with respect to opening 311 is 8 mm. For this reason, antenna device 9 is arranged at a position away by 8 mm from housing body 31 which is formed containing an electrically conductive material such as a carbon fiber, which positioning is preferable to keep the receiving sensitivity and reception gain.

On the same surface as a surface on which antenna device 9 is formed and the surface is a surface of cover body 321, as are shown in FIGS. 1 and 2, recharging terminal 45, which is connected with an external power source and the like when rechargeable battery 25 (refer to FIG. 16 or the like) arranged in the inside of housing 3 is charged, is formed, and further, electric power switch 46 to switch ON/OFF of the power source of cassette type detector 1 is arranged. Further, at the corner formed by a surface on which antenna device 9 is formed and a radiation entering surface, indicator 47, which is structured by, for example, an LED and displays a recharging condition of rechargeable battery 25 or various operation states, is arranged.

In the present embodiment, a part for interface includes above recharging terminal 45, electric power switch 46, indicator 47, and antenna device 9, and means one which is an electronic/electric part, and is arranged outside of detector unit 2.

In the present embodiment, a case where all the above parts for interface are arranged at first cover member 32 is exemplified, but a configuration, in which all of or a part of the above parts are arranged at second cover member 33 or the like, may be accepted. Further, the part for interface is not limited to the above exemplified ones, but may includes other parts, or a configuration which is not provided with a part of them may be accepted.

Figure 3:
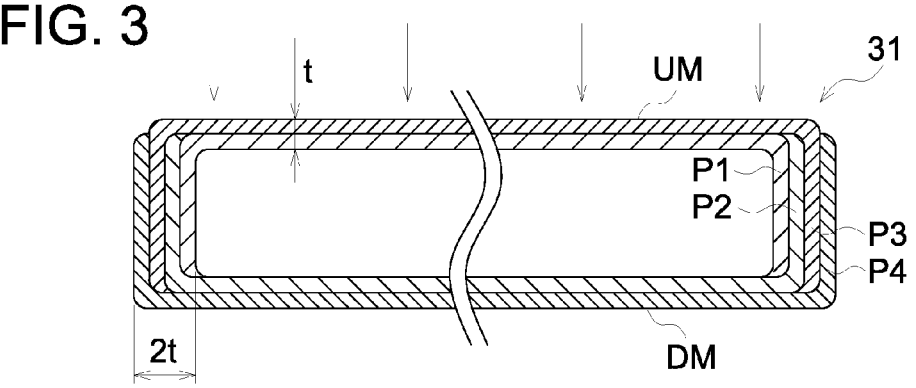
FIG. 3 is a sectional view of the housing body.

Housing body 31 is formed of a carbon fiber in a rectangular tube shape. FIG. 3 is a sectional view of housing body 31 at single-dot chain line IL in FIG. 2, and shows in detail the internal structure of housing body 31. The arrows shown in FIG. 3 indicate the incident direction of radiation in the case where photographing is carried out using cassette type detector 1, and UM and DM indicate the upper wall surface of housing body 31 and the bottom wall surface of housing body 31, respectively.

As it is shown in FIG. 3, housing body 31 is configured as integrated parts of first prepreg P1, second prepreg P2, third prepreg P3, and fourth prepreg P4, and has a four-layered structure (a laminated structure). Each of first prepreg P1, second prepreg P2, third prepreg P3, and fourth prepreg P4 is a carbon fiber in which epoxy resin is impregnated, and, in the present example, the thickness of each prepreg is made equal, but each of or a part of them may be formed with a different thickness.

Figure 4A:
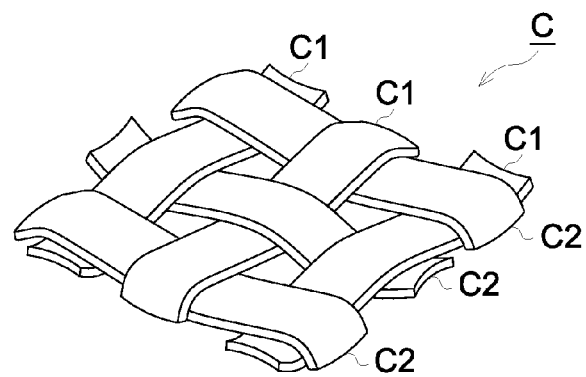
FIGS. 4a and 4b are drawings explaining a structure of a carbon fiber in third prepreg and fourth prepreg.
Figure 4B:
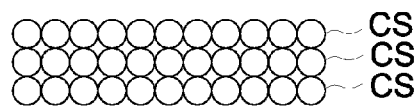

Carbon fiber C in outermost third prepreg P3 and fourth prepreg P4 which contact with a patient or the like is, as it is shown in FIG. 4a, weaved of bundle of carbon fiber C1 which is arranged in one direction and bundle of carbon fiber C2 which is arranged in the orthogonal direction to bundle of carbon fiber C1. FIG. 4b shows a schematic section of bundles of carbon fiber C1 and C2, and bundles of carbon fiber C1 and C2 are configured in a compacted form of a plurality of carbon fiber bundles CS.

By making the structure of carbon fiber in third prepreg P3 and fourth prepreg P4, both of which are the outermost layers of the walls, as shown in FIGS. 4a and 4b, housing body 31 is strengthened, and at the same time splinters of carbon fiber are not likely to be produced due to damage at a time of impact by dropping, and thereby security can be secured.

Figure 5:
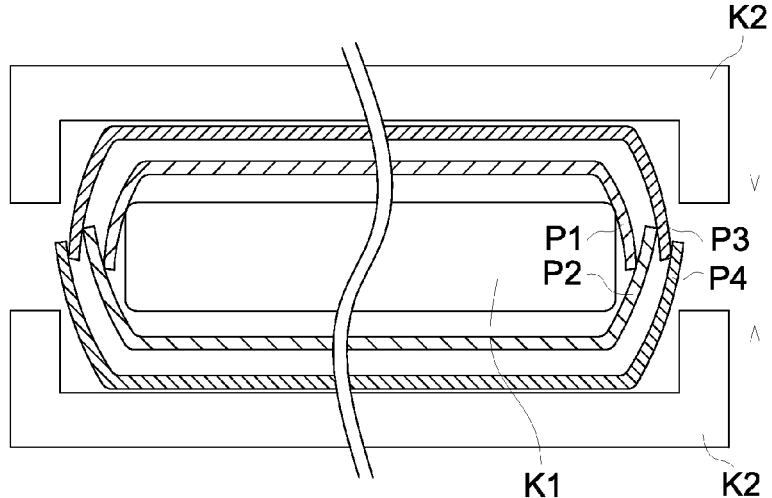
FIG. 5 is a drawing explaining a method for manufacturing the housing body.

Housing body 31 is formed in a manner that, as it is shown in FIG. 5, first prepreg P1, second prepreg P2, third prepreg P3, and fourth prepreg P4 are wound around inner cast K1, and after that, two outer casts K2 are moved in the arrow direction to press and adhere the above prepregs, and then all prepregs are heated with high temperature under high pressure, after that inner cast K1 is pulled out and then, an integrated rectangular tube shape, which is now one piece, is formed.

In housing body 31 which was produced by the method such as shown in FIG. 5, the wall of housing body 31 in the incident direction of radiation which is the wall facing to the incident direction of radiation (in the vertical direction in FIG. 3) is formed of two layers, first prepreg P1 and third prepreg P3, as it is shown in FIG. 3, and the wall of housing body 31 in the perpendicular direction to the incident direction of radiation (in the horizontal direction in FIG. 3) is formed of four layers, first prepreg P1, second prepreg P2, third prepreg P3, and fourth prepreg P4. Therefore, if the thickness of the wall of housing body 31 in the incident direction of radiation is set to t, the thickness of the wall of housing body 31 in the perpendicular direction to the incident direction of radiation becomes doubled, 2t.

When comparing a comparative example of the wall of the housing body (refer to FIG. 6a) in which the thickness in the perpendicular direction to the incident direction of radiation is t with housing body 31 of the present embodiment (refer to FIG. 6b), since the section can be assumed to be a simplified rectangle, section secondary moment I(A) in FIG. 6a is I(A)=t×k (coefficient), and section secondary moment I(B) in FIG. 6b becomes I(B)=2t×k (coefficient). Since deflection $\delta_A$ in FIG. 6a is $\delta_A$=K/I(A), and deflection $\delta_B$ in FIG. 6b becomes $\delta_B$=K/I(B), $\delta_B/\delta_A$ becomes 0.5 ($\delta_B/\delta_A$=0.5), and therefore, when comparing to the comparative example of FIG. 6a, housing body 31 of the present embodiment as it is shown in FIG. 6b shows higher rigidity of about two times.

Housing body 31 having a structure as it is shown in FIG. 3 increases the strength by increasing the thickness of the side surface relating to the strength such as torsion, and warp, while keeping the amount of penetrating radiation, and therefore, a permissible weight of the patient which acts on the cassette type detector 1 when radiographing at full load can be increased. Cassette type detector 1 having no handle has a high possibility that it drops at each marginal end thereof, but the increase in the thickness of the side wall also makes it possible to improve drop resistance properties, and thereby the damage of cassette type detector 1 can be prevented.

In the case where housing body 31 is formed by such method, since the internal circumference of housing body 31 is accurately determined by the outer circumference of inner cast K1, housing body 31 having no variation in sizes can be simply formed, and is preferable for a fitting method of the cover member as it is shown in FIG. 2.

Since housing body 31 after being integrated to one piece can be formed as a seamless integrated structure having different thicknesses, an external force and an external pressure can be dispersed when the impact or the like from the outside is exerted to the housing.

As the carbon fiber which forms housing body 31, pitch-based carbon fiber is preferably used.

FIG. 7 is a table which compares a modulus of elasticity and thermal conductivity of various materials. The carbon fiber includes PAN-based carbon fiber and pitch-based carbon fiber, and as it is shown in FIG. 7, the pitch-based carbon fiber has a modulus of elasticity of more than or equal to three times of the PAN-based carbon fiber, and therefore housing body 31 can obtain a sufficient strength even if the thickness of the wall is decreased. The carbon fiber has generally low thermal conductivity compared to a metal such as aluminum, and then has a problem that, when heat is generated in the housing formed of the carbon fiber, the heat stays in the housing without being radiated.

On this point, since the pitch-based carbon fiber has high thermal conductivity comparable to that of aluminum, even in the case where the inside of housing 3 is provided with a plurality of heat producing parts such as various electronic components 22 and rechargeable battery 25 which will be described later, it is possible for the pitch-based carbon fiber to efficiently radiate generated heat, and therefore an adverse effect on various portions due to the stay of heat in the inside of housing 3 can be prevented.

Figure 16:
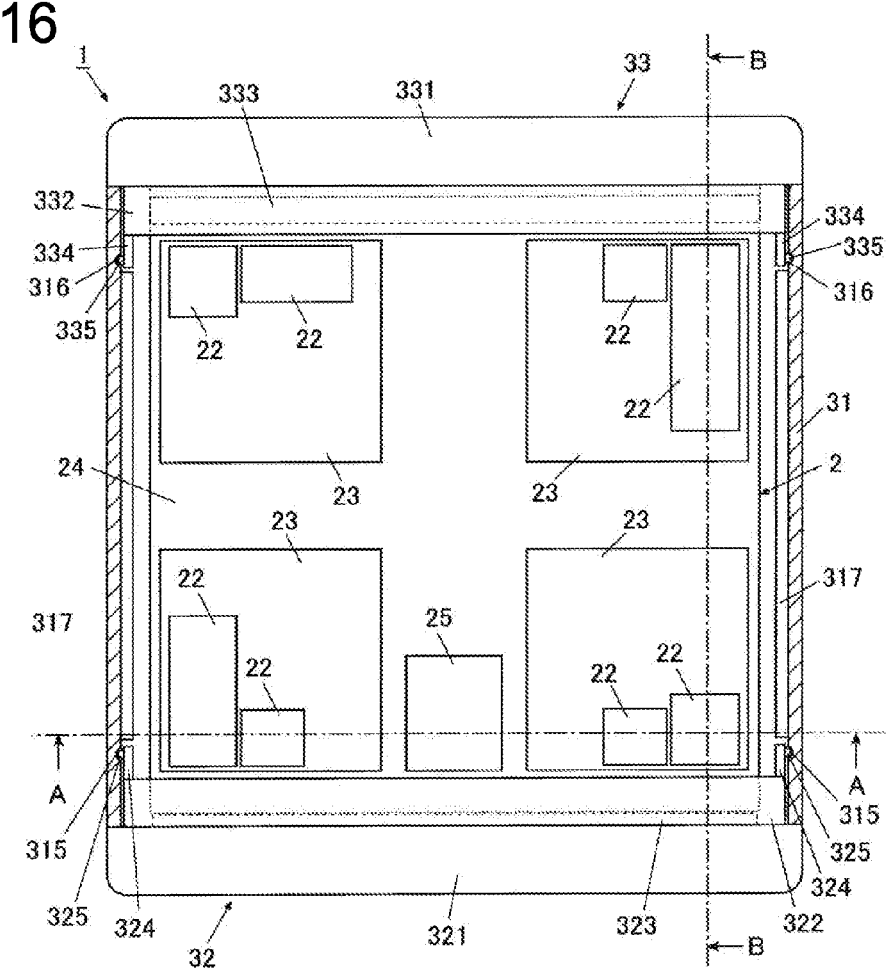
FIG. 16 is a schematic view showing the inside constitution of a cassette type detector shown in FIG. 1.

At positions, which are inside of housing body 31 and correspond to engaging convex parts 325 and 335 of engagement pieces 324 and 334 of each of cover members 32 and 33, as they are shown in FIGS. 2 and 16, engaging concave parts 315 and 316, which engage with engaging convex parts 325 and 335, are formed.

Housing 3 is configured in a manner that, by engaging each of engaging convex parts 325 and 335 with engaging concave parts 315 and 316 by inserting insertion section 322 of first cover member 32 into opening 311 located at one side end portion of housing body 31, and inserting insertion section 332 of second cover member 33 into opening 312 located at the other side end portion of housing body 31, both openings 311 and 312 are blocked and the inside is tightly shut, and thereby housing 3 comes together. The means to connect housing body 31 with each of cover members 32 and 33 is not limited to one exemplified the above, but they may be connected using, for example, screw clamps, or may be fixed with adhesive.

The present embodiment has such a configuration that first cover member 32 and second cover member 33, once the housing was assembled, are firmly fixed to housing body 31, and are impossible to be taken away. Such configuration can close more tightly housing 3. Due to the reason, when, for example, replacement of rechargeable battery 25 is required, cover members 32 and 33 should be broken and cassette type detector 1 should be disassembled, but cover members 32 and 33 which are formed of resin or the like are relatively inexpensive, and therefore, even if they are broken the loss is small. On the other hand, detector unit 2 located inside can be taken away to be reused.

At the both sides of the inside of housing body 31, shock-absorbing members 317 are disposed to protect detector unit 2 so that detector unit 2 does not be damaged by interfering with the inner wall surfaces of housing body 31. The material of shock-absorbing member 317 is not particularly limited, and, for example, resin having elasticity such as silicon, and polyurethane, or the like material can be applied.

In order to stop an effect of a load from the outside (such as weight of the patient) on detector unit 2 which was stored in the inside of housing 3, it is necessary to regulate the deflection amount of the whole cassette type detector 1 so that it should be within the permissible deflection amount of detector unit 2.

The maximum deflection amount of housing 3 of cassette type detector 1 which is assumed when the patient is practically photographed, and stress affecting on glass substrates 213 and 214 which constitute detector unit 2 will be described with reference to data.

FIG. 8 shows a simulation result on the deflection amount of housing 3 of cassette type detector 1.

In this simulation, for housing body 31, a pitch-based carbon fiber having tensile elastic modulus of 790 Gpa as a carbon fiber was used, and cassette type detector 1 having a structure that the height of the side of housing 3 is 8 mm, and the thickness of the wall of housing body 31 is 2 mm was used. As the size thereof, a half-size (14 inch×17 inch) which is most likely to cause deflection was used.

Figure 10:
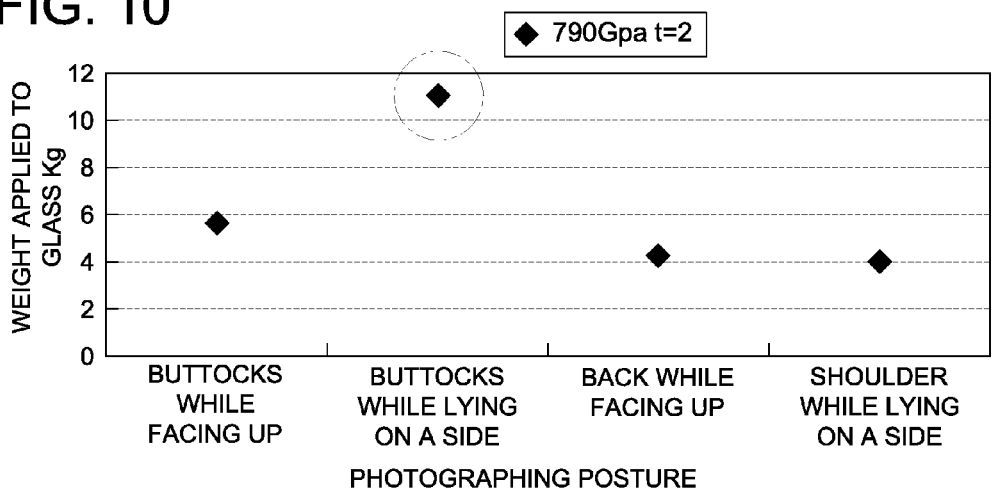
FIG. 10 is a graph showing a weight on a glass substrate for each photographing posture.

The weight applied to cassette type detector 1 depends on a photographing posture, and the photographing posture which exerts the largest weight on cassette type detector 1 among supposable usage environments is a case where the patient lies on his/her side on a bed and cassette type detector 1 is placed under his/her buttock (refer to FIG. 10). Therefore, the simulation shown in FIG. 8 is, in a case of such a photographing posture, carried out regarding a case where cassette type detector 1 placed under the patient is moved.

Figure 9A:
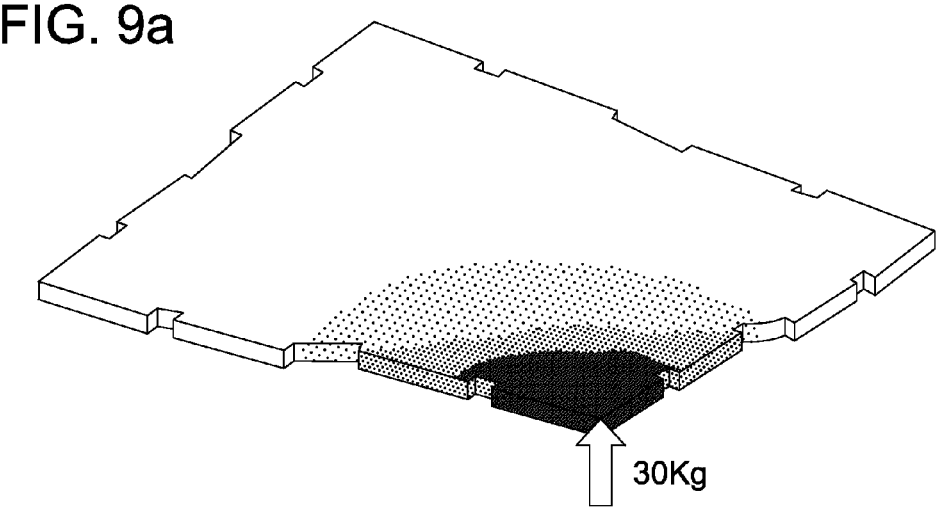
FIGS. 9a and 9b are drawings explaining how a weight works on in the case of supporting a detector in a cantilever fashion.
Figure 9B:
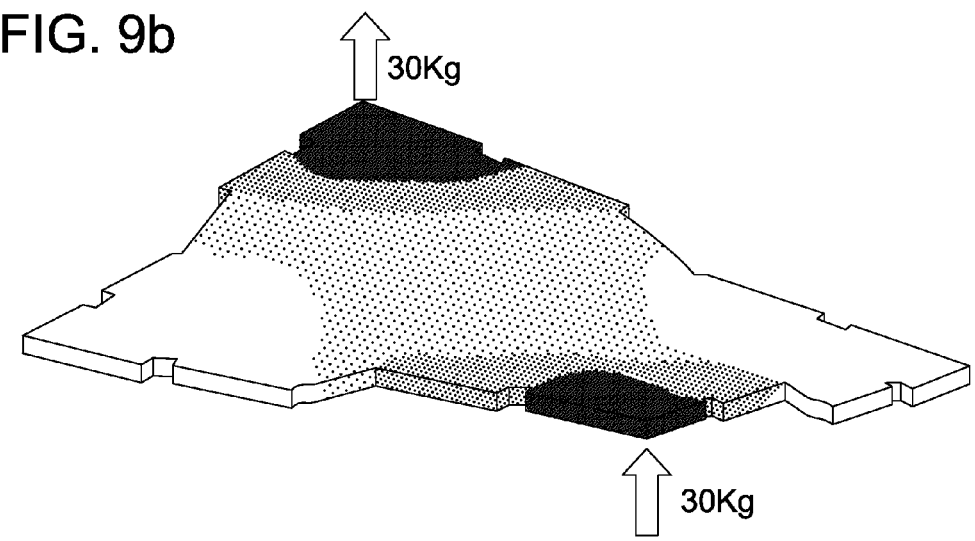

In FIG. 8, pattern 1 shows the maximum deflection amount of cassette type detector 1 of a case, as it is shown in FIG. 9a, to support only one corner of cassette type detector 1 in a cantilever fashion, and to move cassette type detector 1 in a state of having a weight on the top. This is assumed that, for example, cassette type detector 1 is once set under buttock of the patient who lies on his/her side, and then cassette type detector 1 is moved to change the position by one person. Pattern 2 shows the maximum deflection amount of cassette type detector 1 of a case, as it is shown in FIG. 9b, to support diagonal two corners of cassette type detector 1, and to move cassette type detector 1 in a state of having a weight similarly to pattern 1. This is assumed that, for example, cassette type detector 1 is moved by two persons.

Since there was obtained a result of an actual measurement that the maximum weight applied to housing 3 of cassette type detector 1 was about 30 kg when moving cassette type detector 1 which was inserted under the patient who lies on his/her side on a bed, the deflection amount was measured for both patterns 1 and 2 in a state that a weight of 30 kg was applied to a corner where cassette type detector 1 was supported.

As a result, as it is shown in FIG. 8, in either case, the maximum deflection amount of housing 3 of cassette type detector 1 can be made less than 2 mm.

FIG. 10 shows results of measurements, using pressure measuring device 7 (refer to FIG. 11), of the force (the stress) exerted on glass substrates 213 and 214 of detector unit 2 (refer to FIG. 17 or the like), in the case of carrying out photographing by placing cassette type detector 1 on a plate having a relatively high rigidity such as a Bucky.

Pressure measuring device 7 is, for example, as it is shown in FIG. 11, provided with sensor sheet 71 which converts the pressure change added from the outside with a pressure sensitive element into electric signals to output; and computer 73 which receives, through sensor connector 72, the electric signals having been output from sensor sheet 71. Specifically, the measurement was carried out using the I -SCAN SYSTEM, manufactured by Nitta Co. Ltd.

The measurements were carried out in four types of combinations of photographing postures and photographing positions, that is, in two cases where, in a state that the patient lies face up, cassette type detector 1 was placed under his/her buttock, or cassette type detector 1 was placed under his/her back, and in two more cases where, in a state that the patient lies on his/her side, cassette type detector 1 was placed under his/her buttock, or cassette type detector 1 was placed under his/her shoulder. In each case, the pressure applied to housing 3 of cassette type detector 1 was measured by placing sensor sheet 71 of pressure measuring device 7 under the photographing position of the patient.

As it was described above, the photographing posture in which the largest weight is applied to cassette type detector 1 is a case where the patient lies on his/her side on a bed and cassette type detector 1 is placed under his/her buttock. In the case where, for example, photographing of the patient having a weight of 100 kg with such a photographing posture, the maximum weight exerting on glass substrates 213 and 214 of detector unit 2 of cassette type detector 1 become about 11 kg as it is shown in FIG. 10.

As it was described above, the deflection amount (the amount of strain) of housing 3 produced when cassette type detector 1 is supported in a cantilever fashion and is moved is less than or equal to 2 mm, and, on the other hand, the permissible deflection amount of detector unit 2 is 6 mm. Therefore, when the full load photographing, in which the full load of the patient is applied to housing 3, is carried out, even if transfer or position change of cassette type detector 1 which was once set under the patient is carried out, the maximum stress exerting on glass substrates 213 and 214 does not exceed the permissible stress of glass substrates 213 and 214, and thereby failure such as breakage of glass substrates 213 and 214 does not occur.

Namely, as it is shown in FIG. 12, in the case of a glass plate (a glass substrate) of 8 mm or less in thickness, the permissible stress against an instantaneous force (short term permissible stress) worked when cassette type detector 1 is transferred, is 24.5 MPa in the plane of the glass substrate.

In the case where a uniformly-distributed weight is applied in a state that four sides walls of a rectangular board member like glass substrates 213 and 214 are supported, the maximum stress is 23 MPa, and the maximum deflection amount is 6 mm as they are shown in FIG. 13.

Figures 14, 15:
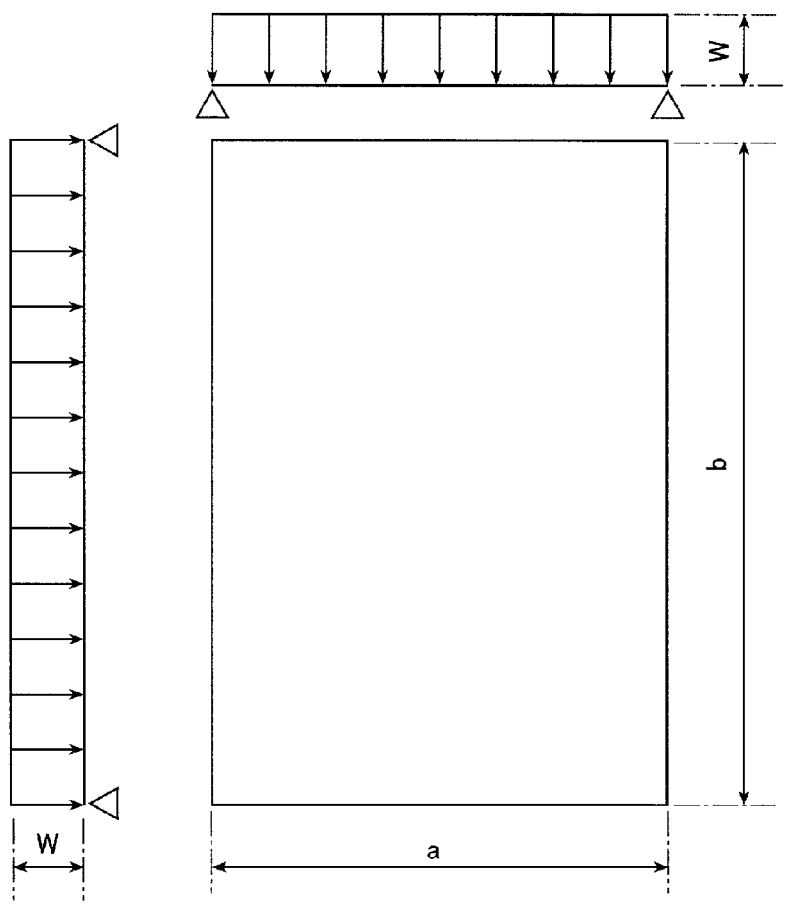
FIG. 14 is a figure explaining a four-side support glass substrate.
FIG. 15 is a table showing a coefficient of a four-side support glass substrate.

The maximum stress and the maximum deflection in FIG. 13 were, as it is shown in FIG. 14, calculated using Formulas (1) and (2) respectively, after coefficients α1 and β1 (refer to FIG. 15) of a case of a side length ratio b/a being 1.2, when the longitudinal direction of the rectangular board member in which the four sides were supported is designated as "b" and the direction perpendicular to the longitudinal direction is designated as "a".

$$\sigma = \beta_1 (W \cdot a^2)/t^2 \quad \text{(Formula 1)}$$

$$\delta = \alpha_1 (W \cdot a^4)/E \cdot t^3 \quad \text{(Formula 2)}$$

As it was described above, the maximum stress produced when the maximum weight, which can be estimated on using cassette type detector 1, was applied, is 23 MPa and the maximum deflection amount is 6 mm, while in the case of a glass plate (a glass substrate) of less than or equal to 8 mm in thickness, such as glass substrates 213 and 214 of the present embodiment, the permissible stress is 24.5 MPa, and an amount of deflection within 6 mm is allowable. Therefore, even in any cases where photographing is carried out with various photographing postures, failure such as breakage of glass substrates 213 and 214, and detector unit 2 comprising them, may not be caused.

Figure 17:
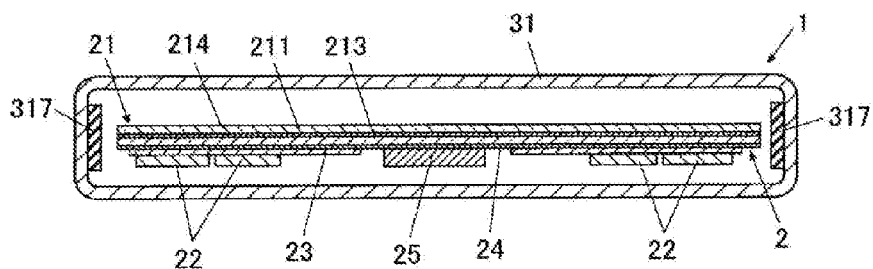
FIG. 17 is the A-A sectional view of FIG. 16.
Figure 18:
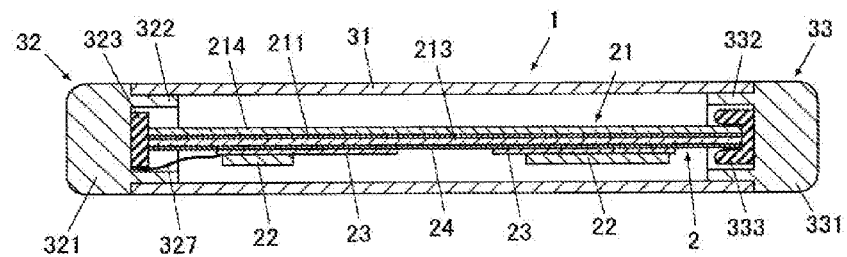
FIG. 18 is the B-B sectional view of FIG. 16.

FIG. 16 is a plan viewed from the upper side (the entering side of radiation at a time of photographing) of housing 3 in which detector unit 2 was stored, FIG. 17 is the A-A sectional view of FIG. 16, and FIG. 18 is the B-B sectional view of FIG. 16. In FIG. 16, for convenience of explanation, the arrangement of each member in the inside of cassette type detector 1 of the case where the upper surface of housing body 31 was removed is schematically shown.

As they are shown in FIGS. 16, 17, and 18, detector unit 2 is configured having detection panel 21, circuit board 23 in which various electronic components 22 are implemented, and the like. In the present embodiment, circuit board 23 is fixed to base 24 which is formed of resin or the like, and, by fixing above base 24 to detection panel 21 using adhesive or the like, circuit board 23 is fixed, through base 24, to detection panel 21. In addition, base 24 is not a constitutional element essential to the present invention, and a configuration may be such that circuit board 23 or the like is directly fixed to detection panel 21 without through base 24.

As it is shown in FIG. 16, in the present embodiment, circuit board 23 which mounts electronic components 22 is divided into four boards, and each of them is arranged near each corner of detection panel 21. Electronic components 22 are arranged on circuit board 23 along the outer circumference of detection panel 21. Electronic components 22 are preferably disposed at positions near each corner of detection panel 21 as much as possible. By disposing electronic components 22 on circuit board 23 in such a manner, when detector unit 2 is stored in housing 3, electronic components 22 are disposed along the (high strength) area which is hard to be deformed against an external force, such as near corners of housing 3 and peripheral of housing body 31. The number of circuit boards 23 or electronic components 22 or the arrangement thereof is not limited to them exemplified in the above.

Figure 23:
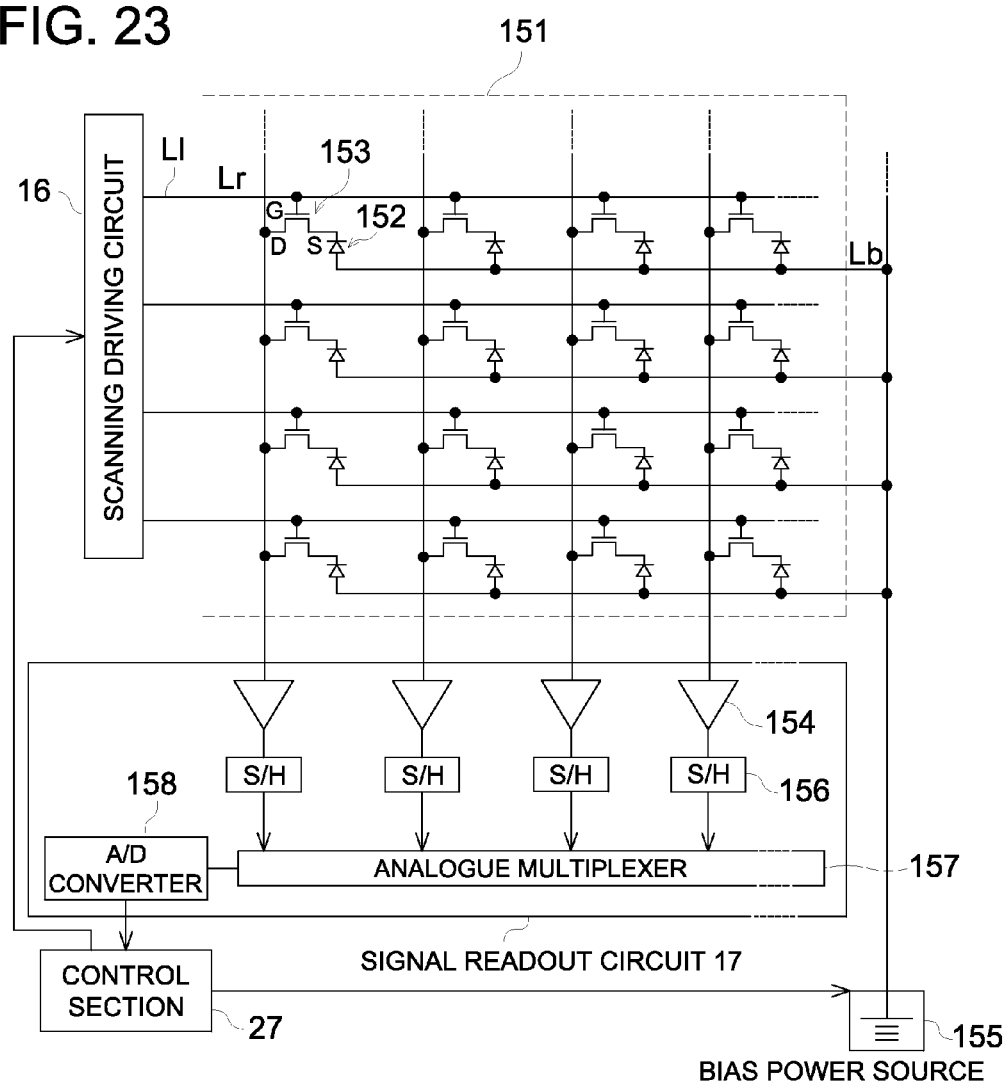
FIG. 23 is a configuration diagram of an equivalent circuit in which the photoelectric conversion section shown in FIG. 22 was arranged two-dimensionally.

In the present embodiment, electronic component 22 disposed on circuit board 23 includes, for example, a CPU (a central processing unit) (not-illustrated) which constitutes control section 27 (refer to FIG. 23) controlling each section; a memory unit (not-illustrated) composed of a ROM (a read only memory) or a RAM (a random access memory); scanning driving circuit 16 (refer to FIG. 23); or signal read out circuit 17 (refer to FIG. 23). Apart from the ROM and RAM, there may be provided with an image memory section which is comprised of a rewritable read only memory such as a flash memory and stores image signals which were output from detection panel 21.

Detector unit 2 is also provided with a communication section (not-illustrated) which sends and receives various signals to and from external equipment. The communication section is designed, for example, to transmit, through above-described antenna device 9, image signals which were output from detection panel 21 to external equipment, or to receive, through antenna device 9, a photographing starting signal or the like which is sent from external equipment.

Further, at a position, on base 24, near recharging terminal 45 which is disposed at first cover member 32 when detector unit 2 is stored in the inside of housing 3, there is disposed rechargeable battery 25 as a power supply section which supplies electric power to a plurality of driving sections which configures cassette type detector 1 (for example, scanning driving circuit 16 which will be described later (refer to FIG. 23), signal read out circuit 17 (refer to FIG. 23), a communication section (not illustrated), a memory section (not illustrated), a charge quantity detection section (not illustrated), indicator 47, and detection panel 21).

As rechargeable battery 25, applicable are chargeable battery such as a nickel-cadmium battery, a nickel-hydrogen battery, a lithium-ion battery, a small sealed lead battery, and a lead storage battery. In addition, in place of rechargeable battery 25, a fuel cell or the like may be applied. The shape, size, the number, arrangement, or the like of rechargeable battery 25 as a power supply section are not limited to those exemplified in FIG. 16 or other figures.

Rechargeable battery 25 is configured to be electrically connected with the above recharging terminal 45 by rechargeable battery 25 being disposed at a prescribed position on base 24, and, for example, it is configured that, by installing cassette type detector 1 in a recharging device (not illustrated) such as a cradle by which cassette type detector 1 is connected to an external power source, a terminal on the recharging device side is connected with recharging terminal 45 on the side of housing 3 to charge rechargeable battery 25 with electricity.

At the end portion of circuit base 23 which is connected with various electronic components 22 and rechargeable battery 25, flexible harness 327 composed of flexible materials is arranged.

Circuit board 23 and the like are electrically connected, by above flexible harness 327, with recharging terminal 45, electrical power switch 46, indicator 47, and antenna device 9 as parts for interface which are disposed on first cover member 32. A method for connecting flexible harness 327 with each of parts for interface of first cover member 32 may include using a connector or soldering.

Figure 19:
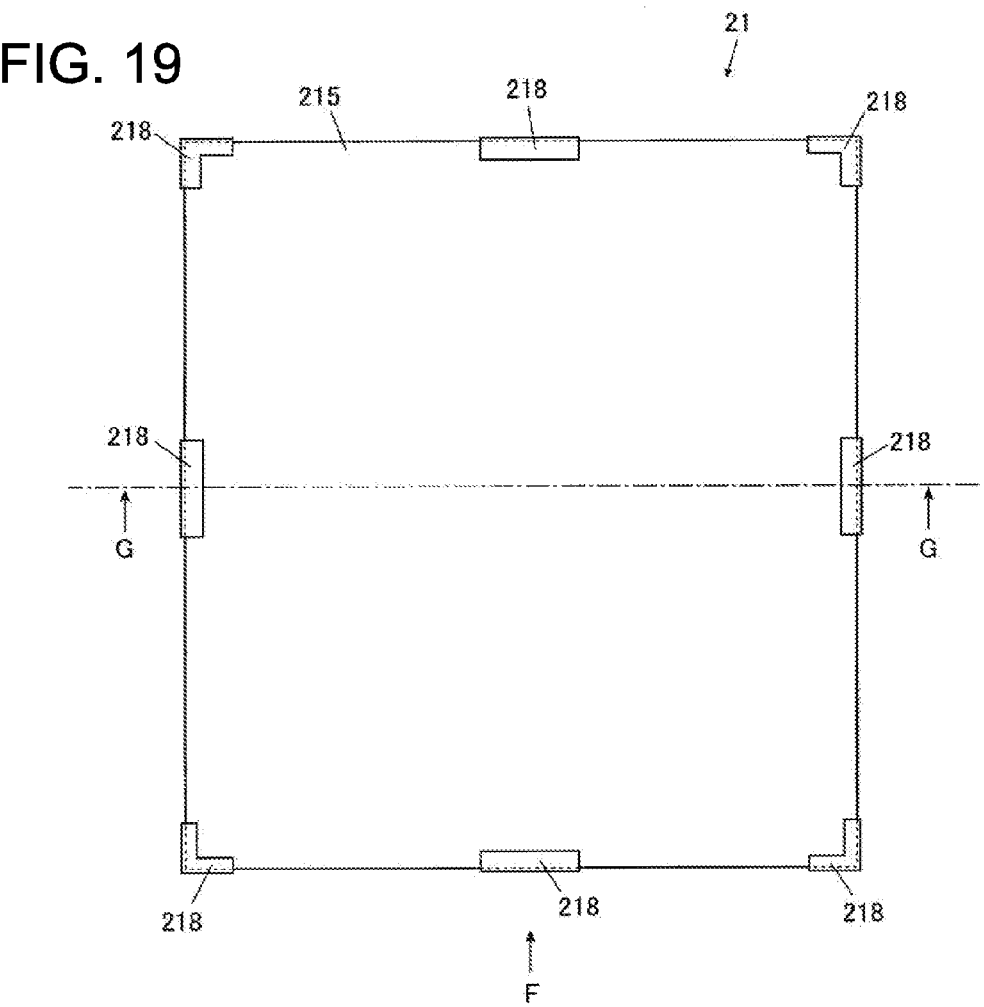
FIG. 19 is a plan view showing the detection panel of the present embodiment.
Figure 20:
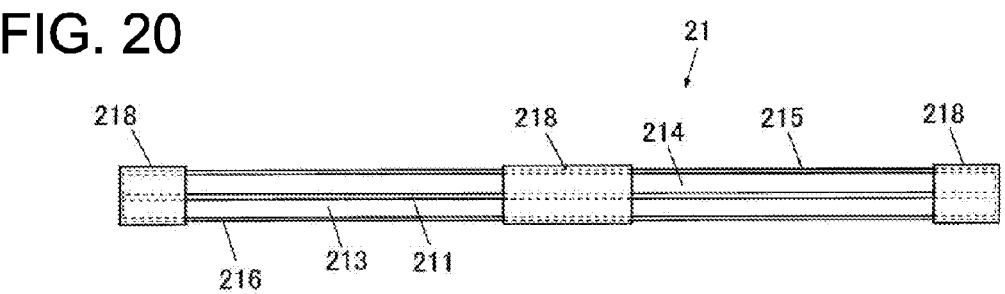
FIG. 20 is a side view of the detection panel shown in FIG. 19 viewed from the direction of arrow F.
Figure 21:
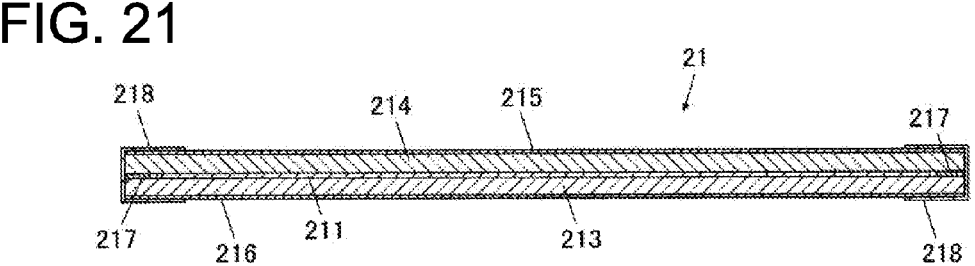
FIG. 21 is the G-G sectional view of the detection panel shown in FIG. 19.

FIG. 19 is a plan view of detection panel 21, FIG. 20 is a side view of detection panel 21 viewed from the direction of arrow F in FIG. 19, and FIG. 21 is the G-G sectional view in FIG. 19 of detection panel 21.

Detection panel 21 is configured having first glass substrate 214, in which scintillator layer (light emission layer) 211, as a scintillator which converts incident radiation into light, is formed on one surface thereof, and second glass substrate 213, in which signal detection section 151 which is laminated under scintillator layer 211 and detects converted light by scintillator layer 211 to convert it into electrical signals, is formed on one surface thereof, and has a laminated structure in which the above substrates are laminated.

Scintillator layer 211 has, for example, a phosphor as a major component, and is configured to output electromagnetic waves of 300 nm to 800 nm in wavelength depending on incident radiation, that is, electromagnetic waves (light) covering from ultraviolet light to infrared light, centering around visible light.

As the phosphor used far above scintillator layer 211, usable are, for example, the one in which $CaWO_4$ or the like is a matrix material, or ones in which a light emission center material is activated in matrix materials such as CsI:Tl, $Cd_2O_2S$:Tb, ZnS:Ag, or the like. In addition, if a rare-earth element is designated as M, a phosphor represented by a general formula of $(Gd, M, Eu)_2O_3$ can be used. In particular, due to high radiation absorption or emission efficiency, CsI:

Tl, or $Cd_2O_2S$:Tb is preferable, and, with these matrix materials, a high quality image with low noise can be obtained.

Scintillator layer 211 is made by forming a phosphor layer, using for example vapor deposition, on a support (not illustrated) formed of a variety of high molecular materials (a polymer) such as, for example, cellulose acetate film, polyester film, and polyethylene terephthalate film. The phosphor layer is composed of phosphor columnar crystals. As the vapor deposition, vapor deposition, sputtering, chemical vapor deposition (CVD), or the like is preferably used. Any one of the above methods can perform a vapor-phase growth of the phosphor layer on a support into independent long and narrow columnar crystals.

Scintillator layer 211 is pasted to the underside of first glass substrate 214 (the opposite side of incident radiation at photographing), and glass protection film 215 is further laminated on the upper side of first glass substrate 214 (the incident radiation side at photographing).

On the underside of scintillator layer 211 (the opposite side of incident radiation at photographing), second glass substrate 213 is laminated, and, on the underside of second glass substrate 213, glass protection film 216 is further laminated.

Both of first glass substrate 214 and second glass substrate 213 are of about 0.6 mm in thickness, and by cutting the edge faces of the glass substrates by laser, the edge faces, that is, the cut surfaces, the ridgeline between the cut surface and the upper surface of the glass substrate, and the ridgeline between the cut surface and the bottom surface of the glass substrate are subjected to smoothing treatment. The thickness of first glass substrate 214 and second glass substrate 213 is not limited to 0.6 mm, and first glass substrate 214 and second glass substrate 213 may have a different thickness.

The smoothing treatment by cutting the edge faces of first glass substrate 214 and second glass substrate 213 by laser will be described below.

In the case of cutting glass, it is common to undergo two processes: at first, a vertical crack in the thickness direction of the glass by streaking (scratching) the glass surface with a hard and sharp cutter (a scribing work) is formed, and then the glass is broken by applying stress so as to extend the crack (a cutting in halves work). Heretofore, a streaking work on the glass surface (a scribing work) has been carried out using cemented carbide, electrodeposited diamond, sintered diamond, or the like. However, there was a problem that, in the case where the surface of a glass was scratched with cemented carbide or diamond, fine irregularity was formed on the edge surfaces which was cut (being cut in halves), and when a load such as bending was applied to the glass, the glass was likely to be broken, since stress was concentrated on the above irregularity.

In this regard, in the present embodiment, the scratching work (the scribing work) on the surfaces of first glass substrate 214 and second glass substrate 213 is carried out using laser. In the case where laser is used in this manner, since the edge surface of the glass after it was cut (being cut in halves) is smoothed, strength of glass against load such as bending can be increased.

The breakage of the glass substrate is caused by a partial burr which becomes a center of stress concentration when a glass substrate is cut, or by formation of partial irregularity, rather than the magnitude of external force. Therefore, the smoothing treatment on the edge surfaces in such a manner can prevent generation of breakage or the like of the glass substrate against considerable external force (stress).

As a cutting device to cut the edge surfaces of first glass substrate 214 and second glass substrate 213 by laser, preferably used is, for example, YAG laser or the like in which YAG (a yttrium aluminum garnet crystal) is used as the laser optic medium in the laser oscillation unit, but the cutting device used for cutting is not limited to them.

On the upper side of second glass substrate 213 (the side facing scintillator layer 211), signal detection section 151 is formed which is a detection section to output image signals based on accumulated electric energy, in which electromagnetic waves (light) output from scintillator layer 211 are converted into electric energy which is then accumulated.

In this way, the present embodiment has a structure such that signal detection section 151 is laminated under scintillator layer 211, and signal detection section 151 and scintillator layer 211 arc sandwiched in a opposed state between second glass substrate 213 disposed under signal detection section 151 and first glass substrate 214 disposed over scintillator layer 211.

Heretofore, it has been assumed that, if the stress worked on a glass substrate, which is located inside the housing, is not restrained through a housing, the breakage of the glass substrate cannot be prevented, and therefore the spaces between the housing and the glass substrate were arranged, and many buffer members, which ease or decrease the external force, were used in the aforesaid spaces, which configuration makes the housing further larger size.

In this regard, the inventors found that the breakage of the glass substrate is caused by a partial burr which becomes a center of stress concentration when a glass substrate is cut, or by formation of partial irregularity, rather than the magnitude of external force worked on the aforesaid glass substrate. Then, to remove the above burr which becomes the above center of stress concentration, or irregular portions, the inventors carried out smoothing treatment on the edge surfaces generated after cutting, and due to the treatment, it became possible to prevent generation of breakage or the like of glass substrates 213 and 214 against a load or bending caused by weight of the patient or the like which works on housing 3 having the configuration such as described above.

Further, sealing member 217 is disposed along periphery edges of first glass substrate 214 and second glass substrate 213, and, with this sealing member 217, first glass substrate 214 and second glass substrate 213 are bonded and connected. With this configuration, the strength against a load such as bending can be increased.

Further, it is designed such that, when bonding first glass substrate 214 to second glass substrate 213, the bonding and connection with sealing member 217 are carried out after deaerating the space between first glass substrate 214 and second glass substrate 213 by absorbing air. With this design, it becomes possible to prevent moisture contained in air to affect scintillator layer 211 or the like, resulting in extension of life of scintillator layer 211 or the like.

In addition, buffer member 218 to protect detection panel 21 from external impact or the like is arranged at each corner of detection panel 21 and near intermediate portions between the corners.

Figure 22:
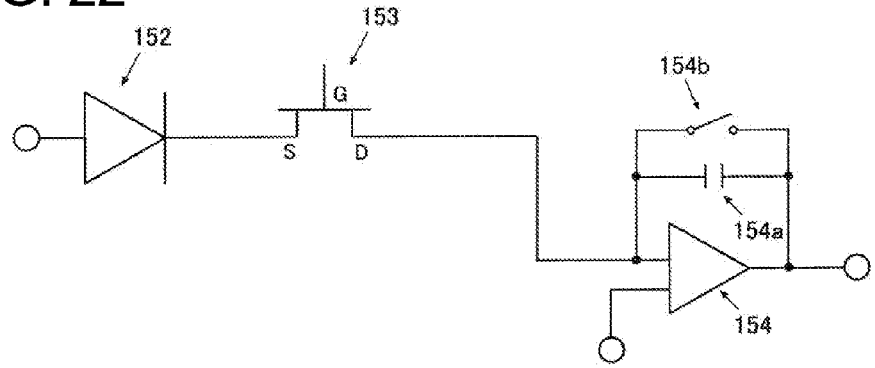
FIG. 22 is a configuration diagram of an equivalent circuit of one pixel of a photoelectric conversion section constituting a signal detection section.

The circuit architecture of detection panel 21 will be described below. FIG. 22 is a diagram of an equivalent circuit of one pixel of a photoelectric conversion section constituting signal detection section 151.

As it is shown in FIG. 22, the configuration of one pixel of a photoelectric conversion section is configured with photodiode 152 and thin-film transistor (hereinafter it is referred to as TFT) 153 which takes out electric energy as electric signals accumulated in photodiode 152 by switching.

Photodiode 152 is an imaging element to generate charges and accumulate them. It is designed such that the electric signals taken out of photodiode 152 are amplified by amplifier 154 to a level where signal read-out circuit 17 becomes detectable.

Specifically, it is designed such that photodiode 152 generates charge when illuminated with light, and when a signal read-out voltage is applied to gate G of TFT 153, the charge flows from photodiode 152 connected to source S of TFT 153 to drain D of TFT 153, which charge is then accumulated in condenser 154a which is connected in parallel with amplifier 154, and then, electric signals amplified in proportion to the accumulated charge in condenser 154a are output from amplifier 154.

It is further configured such that, when electric signals amplified by amplifier 154 are output, and the electric signals are taken out, switch 154b, which is connected in parallel with amplifier 154 and condenser 154b, becomes ON to release charge which was accumulated in condenser 154a, and thereby amplifier 154 is reset. Photodiode 152 may be simply a photodiode having a controlled capacitance, or may incorporate in parallel with an additional condenser so as to improve the dynamic range of photodiode 152 and the photoelectric conversion section.

FIG. 23 is a diagram of an equivalent circuit in which such photoelectric conversion section was arranged two-dimensionally, and scanning lines L1 and signal lines Lr are arranged to intersect at right angles among pixels. One end of above photodiode 152 is connected to source S of TFT 153, and drain D of TFT 153 is connected to signal line Lr. On the other hand, the other end of photodiode 152 is connected to the other end of adjacent photodiodes 152, which are disposed at each line, and is connected to bias power source 155 through common bias line Lb.

It is designed such that bias power source 155 is connected to control section 27, and by an instruction from control section 27, a voltage is applied to photodiode 152 through bias line Lb. Gates G of TFTs 153 which are disposed at each line are connected to common scanning line L1, and scanning line L1 is connected to control section 27 through scanning driving circuit 16. Similarly, drains D of TFTs 153 which are disposed at each column are connected to common signal line Lr, and are connected to signal read out circuit 17 which is controlled by control section 27.

In signal read out circuit 17, amplifier 154 is disposed at each above signal line Lr. When a signal is read out, a voltage for a signal read out is applied to selected scanning line L1, and then a voltage is applied to gate G of each TFT 153 which is connected to above scanning line L1, and thereby current generated at photodiode 152 flows from each of above photodiodes 152 to each signal line Lr through each TFT 153. Then, an electric charge is amplified at each amplifier 154 for each photodiode 152, and information of photodiodes 152 located in one line is taken out. Then, it is designed so that, by carrying out the operations for all scanning lines L1 by changing over to each scanning line L1, information from all photodiodes 152 can be taken out.

To each amplifier 154, there is connected each of sample hold circuits 156. It is designed such tat each sample hold circuit 156 is connected to analogue multiplexer 157 which is disposed at signal read out circuit 17, and the signal which was read out by signal read out circuit 17 is output from analogue multiplexer 157 to above control section 27 through A/D converter 158.

TFT 153 may be made of either an inorganic semiconductor or an organic semiconductor, which are used for the liquid crystal display.

In the present embodiment, there was exemplified a case where photodiode 152 as a photoelectric conversion element was used as an imaging element, but, as a photoelectric conversion element, a solid-state image sensing device except for a photodiode may be used.

On the side of above signal detection section 151, there are disposed scanning driving circuit 16 which sends a pulse to each photodiode (a photoelectric conversion element) 152 to scan and drive aforesaid each photodiode 152, and signal read out circuit 17 which reads out electric energy accumulated in each photoelectric conversion element.

Next, functions of cassette type detector 1 of the present embodiment will be described.

In the present embodiment, at first, second glass substrate 213, in which signal detection section 151 is formed on the one surface thereof, and first glass substrate 214, in which scintillator layer 211 was bonded on the one surface thereof, are laminated so that scintillator layer 211 faces signal detection section 151, and after deaeration processing of the space between first glass substrate 214 and second glass substrate 213 was carried out, both glass substrates 213 and 214 are bonded and connected to each other using sealing member 217. Next, base 24, in which circuit board 23, on which various electronic components 22 are disposed, and rechargeable battery 25 are loaded at the predetermined positions, is fixed to the back side of first glass substrate 214 so that the side of base 24 on which circuit board 23 and rechargeable battery 25 are loaded becomes the bottom side. With this configuration, detector unit 2 is completed.

After the completion of detector unit 2, electronic components 22 and rechargeable battery 25, both of which are connected to circuit board 23 of detector unit 2, are electrically connected, using flexible harness 327, to recharging terminal 45, electric power switch 46, indicator 47, and antenna device 9, all of which are disposed on first cover member 32.

Next, in the inside of housing body 31, a non-illustrated jig is disposed which supports detector unit 2 from the underside and guides it when detector unit 2 is inserted. The jig may have, for example, a stick shape or a board shape.

When fitting first cover member 32 into opening 311 of housing body 31, first cover member 32 and detector unit 2, which was connected by flexible harness 327, are inserted from opening 311, and then, detector unit 2 is allowed to slide on the jig while it is pressed by first cover member 32, to be stored in housing body 31.

First cover member 32 is pushed until engaging convex part 325 of engagement piece 324 engages with engaging concave part 315 of housing body 31, which completes the installation of first cover member 32.

Figure 24A:
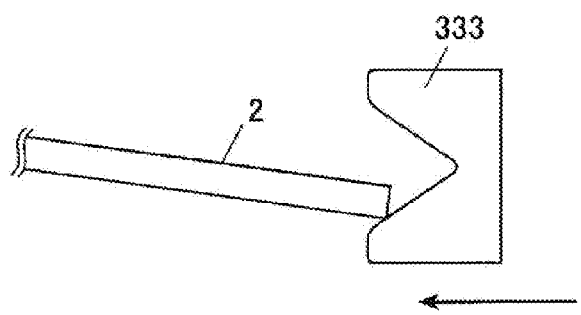
FIG. 24a is a figure showing a state of a detection unit which is struck by a slant of a shock-absorbing member.
Figure 24B:
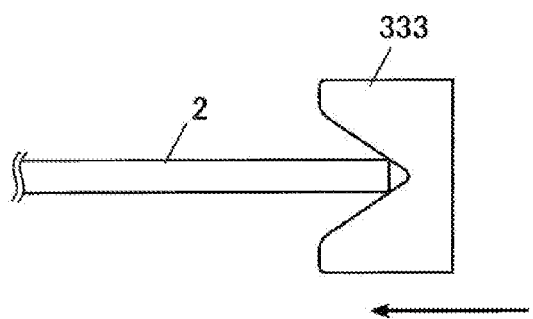
FIG. 24b is a figure showing a state of a detection unit moved to a horizontal position guided by a slant of a shock-absorbing member.
Figure 24C:
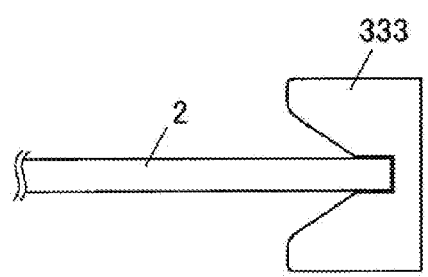
FIG. 24c is a figure showing a state of a detection unit supported by a shock-absorbing member.

When the storing of detector unit 2 and the installation of first cover member 32 are completed, second cover member 33 is fitted into opening 312, after the jig is taken out from opening 312 of housing body 31. At this time, when the end portion of detector unit 2 is inserted with the end portion slanted downward due to its weight, the end portion of detector unit 2 hits against the slant of buffer member 333. At this time, if second cover member 33 is further pushed, the end portion of detector unit 2 is guided along the slant of the end portion of buffer member 333 to the horizontal position as it is shown in FIG. 24b. Then, if second cover member 33 is pushed to the position where engaging convex part 335 of engagement piece 334 engages with engaging concave part 316 of housing body 31, housing 3 becomes an integrated one-piece unit in a state that the inside thereof is tightly closed, and at the same time, the shape of buffer member 333 is deformed in accordance with the shape of the end portion of detector unit 2, and thereby the end portion of detector unit 2 is supported by buffer member 333, as it is shown in FIG. 24c.

With this, one end portion of detector unit 2 is supported by buffer member 323 which is disposed at the side of first cover member 32, and the other end portion of detector unit 2 is supported by buffer member 333 which is disposed at the side of second cover member 33. In this way, it is designed such that, since only the both end portions of detector unit 2 are supported, and therefore there are spaces in the top and bottom directions of detector unit 2, impacts from the top and bottom directions are absorbed by the spaces, and then, the external force is not directly transferred to detector unit 2.

In the case where cassette type detector 1 is used for photographing, for example, the patient, a photographing subject, is put in bed, and cassette type detector 1 is inserted between the bed and the patient with the side where scintillator layer 211 is disposed facing upward, and then photographing is carried out. Further, it is possible to use cassette type detector unit 1 with setting it to a Bucky which is used at photographing using an existing cassette for the CR.

As it was described above, according to the present embodiment, since housing body 31 of cassette type detector 1 is formed in a seamless rectangular tube shape of solid casting, it has such strength in all directions that it is endurable for the practical photographing of the patient though it is a thin type (being less than or equal to 15 mm in thickness), and at the same time, since the size thereof is within JIS standard for a cassette used for a conventional screen/film system, existing apparatuses and facilities, such as a Bucky which is provided for a cassette used for CR, can be used even in the case where a photographing is carried out using cassette type detector 1, which is a cassette type FPD.

Further, since housing 3 of cassette type detector 1 has few joints formed by parts which structure the housing, the possibility of entering dust, sweat of the patient, water from an antiseptic solution or the like, or foreign matter into the housing is decreased, and thereby damage on electric parts can be suppressed due to suppression of deformation of housing 3, and at the same time, longer life of electronic components or the like in the inside of the housing can be achieved.

Cassette type detector 1 is required to have rigidity (strength) against a load, since a load such as the weight of the patient or the like is applied thereto. However, in the present embodiment, detection panel 21 has such a configuration that scintillator layer 211 and signal detection section 151 are sandwiched by two glass substrates (first glass substrate 214 and second glass substrate 213), and at the same time, glass substrates 213 and 214 have high flexural rigidity (flexural strength), since the end surfaces of above glass substrates 213 and 214 are subjected to smoothing processing by cutting them with a laser.

In addition, in the present embodiment, the insertion of detector unit 2 into housing body 31 is completed by electrically connecting in advance detector unit 2 with first cover member 32, and then, fitting first cover member 32 into opening 311, and further the assembly of housing 3 is completed by fitting second cover member 33 into opening 312. Therefore, in the production processes in a plant, works can be efficiently carried out, and at the same time, strictness of accuracy on assembling of detector unit 2 is not so much needed, and thereby an improved yield can be expected.

Since scintillator layer 211 and signal detection section 151 are sandwiched by two glass substrates (first glass substrate 214 and second glass substrate 213), scintillator layer 211 and signal detection section 151 can be prevented from breakage when a load is applied from the outside.

Since the space between first glass substrate 214 and second glass substrate 213 is deaerated, scintillator layer 211 can be prevented from corrosion due to moisture contained in air.

In the present embodiment, since antenna device 9 is disposed at a position at least 6 m away from a member (housing body 31) formed of an electric conductive material, receiving sensitivity and reception gain of antenna device 9 can be maintained high.

Figure 25:
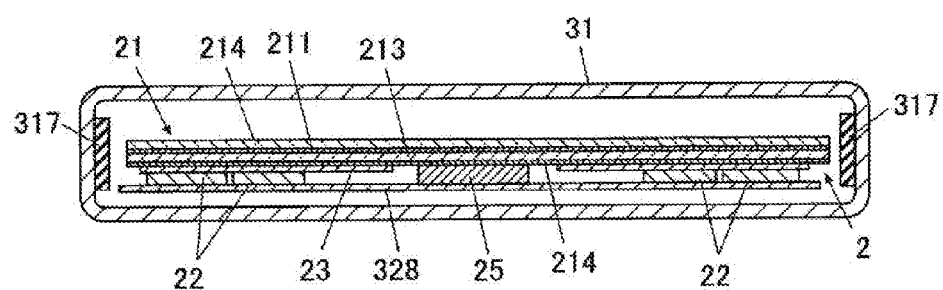
FIG. 25 is a sectional view showing a modified example of the cassette type detector shown in FIG. 1.
Figure 26:
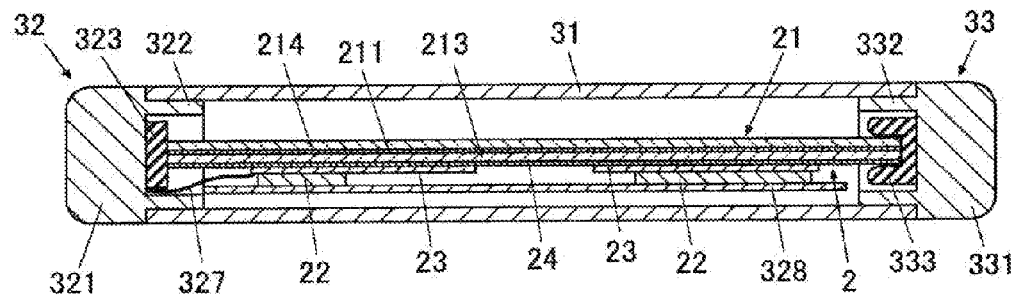
FIG. 26 is a sectional view showing a modified example of the cassette type detector shown in FIG. 1.

In the present embodiment, when detector unit 2 was inserted into housing body 31, it was designed to guide detector unit 2 using a jig, but, for example, as they are shown in FIGS. 25 and 26, support member 328, which supports detector unit 2, was disposed at first cover member 32, and detector unit 2 may be inserted into housing body 31, while detector unit 2 is placed on above support member 328.

Figure 27:
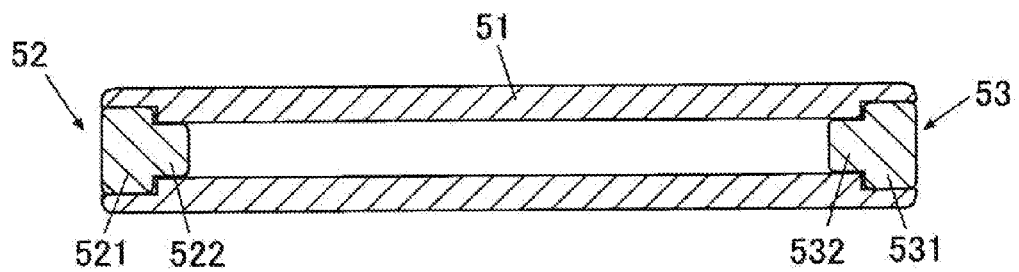
FIG. 27 is a sectional view showing a modified example of an engaged part between a cover member and a housing body of the cassette type detector shown in FIG. 1.

The shape of first cover member 32 and second cover member 33 is not limited to the shape exemplified in this embodiment. For, example, as it is shown in FIG. 27, the shape may be such that both cover bodies 521 and 531 of each cover members 52 and 53 and inserting portions 522 and 532 are fitted into the inside of housing body 51.

Figure 28:
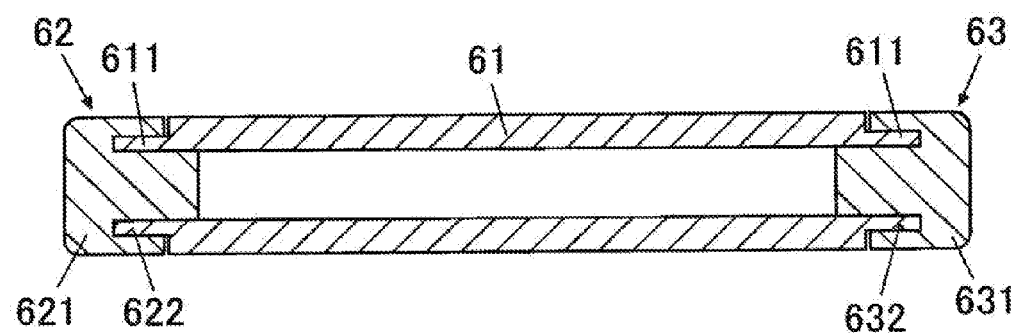
FIG. 28 is a sectional view showing a modified example of the cassette type detector shown in FIG. 1.

Further, as is shown in FIG. 28, gutters 622 and 632 are arranged at cover bodies 621 and 631 of each of cover members 62 and 63, and at the same time, as an engaging means, inserting parts 611 are arranged at each of opening end portions of housing body 61, and then, each of cover members 62 and 63 may be engaged with housing body 61 by inserting above inserting parts 611 into gutters 622 and 632.

Figure 29A:
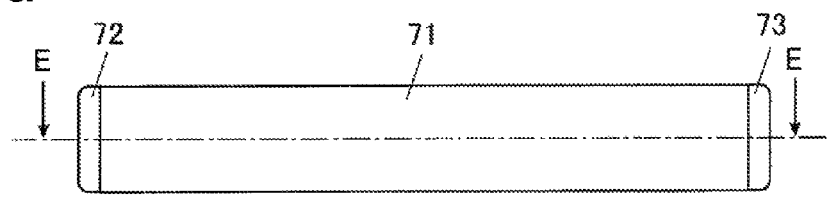
FIG. 29a is a side view showing a modified example of the cassette type detector shown in FIG. 1.
Figure 29B:
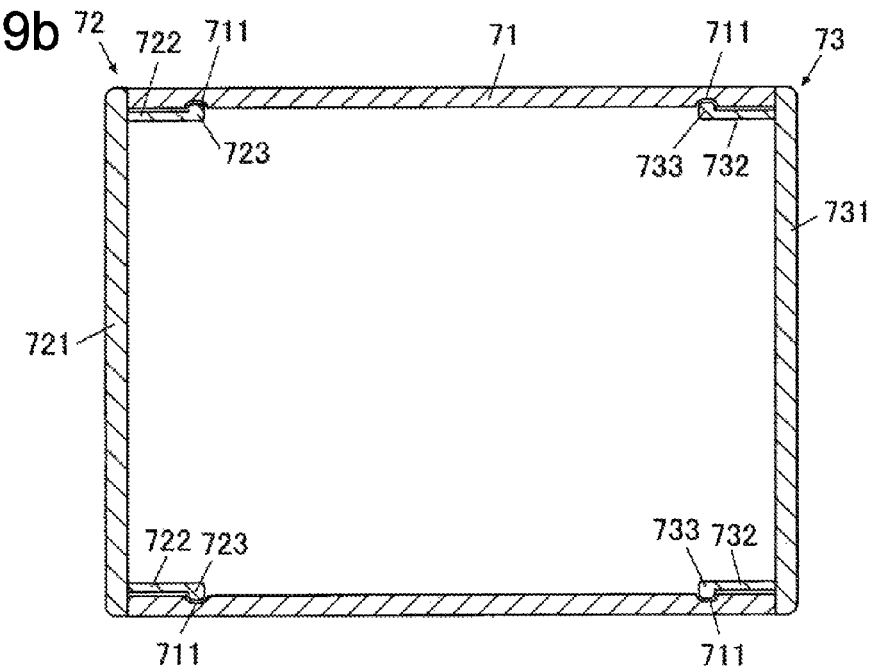

Furthermore, as it is shown in FIGS. 29*a* and 29*b*, without installing the inserting part at each of cover members 72 and 73, engagement pieces 722 and 732, as an engaging means, are directly installed at cover bodies 721 and 731, and then, by making engagement between engaging convex parts 723 and 733 installed at above engagement pieces 722 and 732 and engaging concave parts 711 which were formed in the inside of housing body 71, each of cover members 72 and 73 may be engaged with housing body 71.

The present embodiment has such a configuration that first cover member 32 and second cover member 33 are adhered to housing body 31, and then, once assembly was completed, each of cover members 32 and 33 cannot be removed without braking them, but the configuration may be such that first cover member 32 and second cover member 33 are attachably and detachably mounted on housing body 31. In this case, the configuration is, for example, such that the engaging concave part of the housing body is made to be a through-hole which passes through from the inside of the housing body to the outside, and this through-hole is covered with a seal or the like from the outside. Once assembly was completed, in order to remove the first and second cover members, after the engagement is released by removing the seal and inserting a stick or the like through the through-hole, and pushing out the engaging convex part, the first and second cover members are taken away from the housing body.

Figure 30:
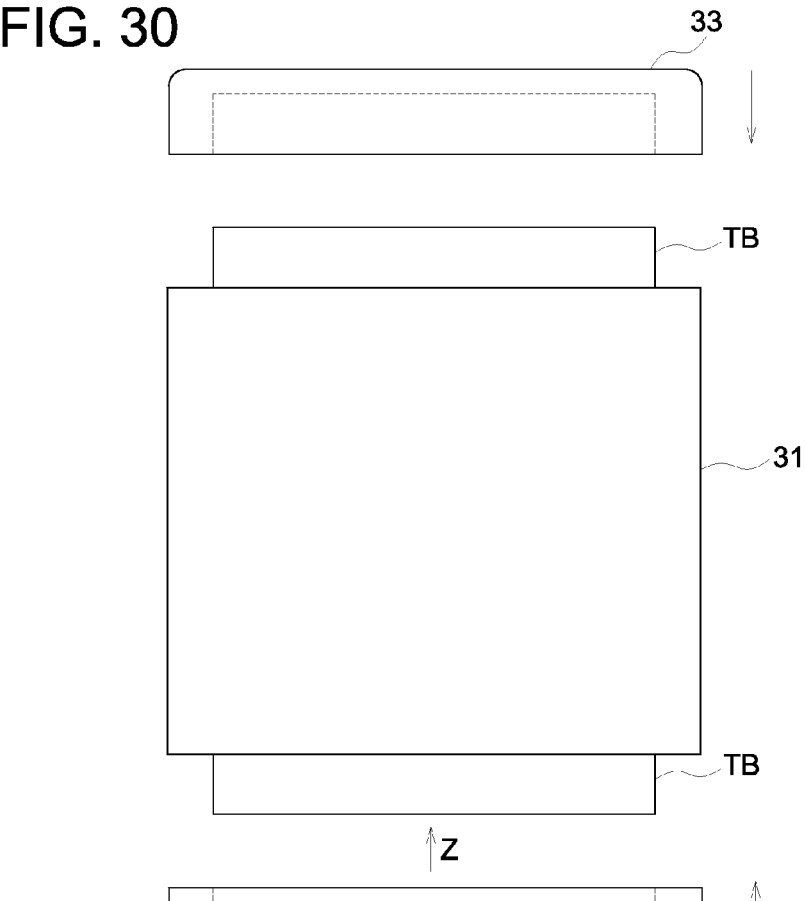
FIG. 30 is a top view showing a modified example of a housing.
Figure 31:
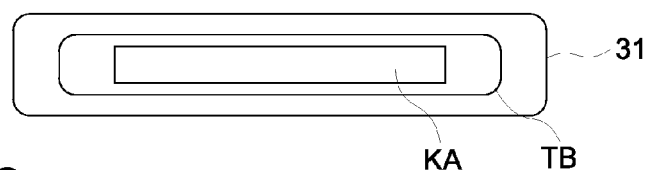
FIG. 31 is a side view showing a modified example of a housing.
Figure 32:
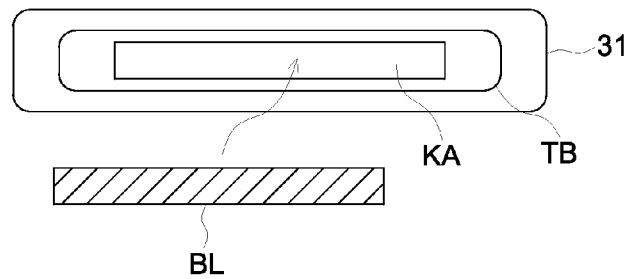
FIG. 32 is a side view showing a modified example of a housing.

Unlike the structure of the housing shown in FIG. 2, the housing may have the structures shown in FIGS. 30 to 32. FIG. 30 is a top view showing a modified example of the housing, and FIGS. 31 and 32 are side views showing modified examples of housing body 31 viewed from the direction of arrow Z shown in FIG. 30.

In the modified example shown in FIG. 30, flanges 113 are formed at the both ends of housing body 31, and, as it is shown in FIGS. 31 and 32, opening KA is formed at the central portion of flange TB. In order to cover opening KA of housing body 31 with first cover member 32 and second cover member 33, first cover member 32 and second cover member 33 are telescoped into flanges TB by moving them in the direction of the arrow indicated in FIG. 30.

As it is shown in FIG. 30, by installing flanges TB at the both ends of housing body 31, it becomes possible to further prevent dust, sweat of patience, water from an antiseptic solution, or the like, or foreign matter from entering into the inside of housing body 31. As it is shown in FIG. 32, strength of flange TB may be increased by filling metallic reinforcing member BL in opening KA.

Figure 33:
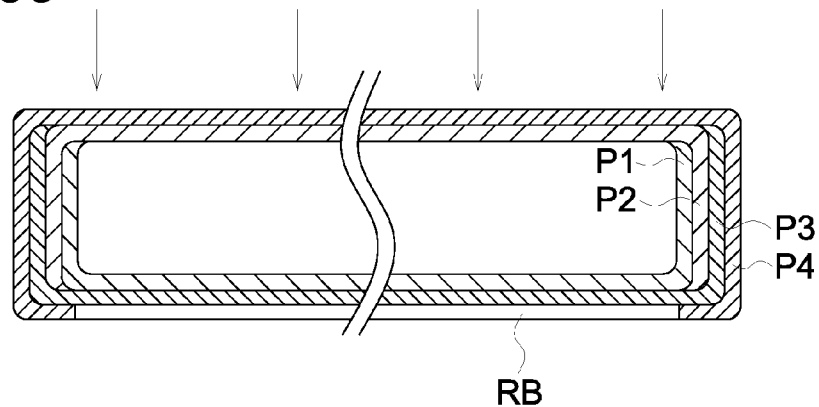
FIG. 33 is a sectional view showing a modified example of the housing body.

The structure of housing body 31 is not limited to the one shown in FIG. 3, and other structures may be allowed. For example, as it is shown in FIG. 33, housing body 31 except for a part of the undersurface is wound around by fourth prepreg P4, the outermost layer, and marking label RB may be bonded with reference to the concavity formed at the undersurface.

Figure 34:
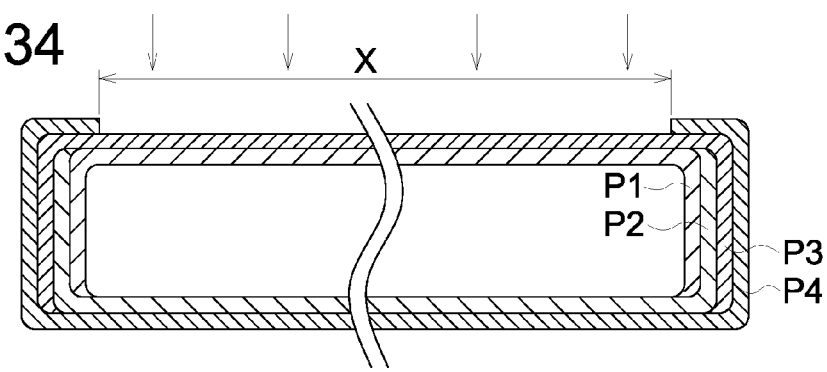
FIG. 34 is a sectional view showing a modified example of the housing body.

As it is shown in FIG. 34, housing body 31 except for a part of the top surface is wound around by fourth prepreg P4, the outermost layer, and the concavity formed at the top surface is allowed to agree with effective photographing region X of radiation. In this way, a radiologist can make excellent photographing operations after the radiologist observes the concavity formed at the top surface to accurately set cassette type detector 1 for the patient.

Figure 35:
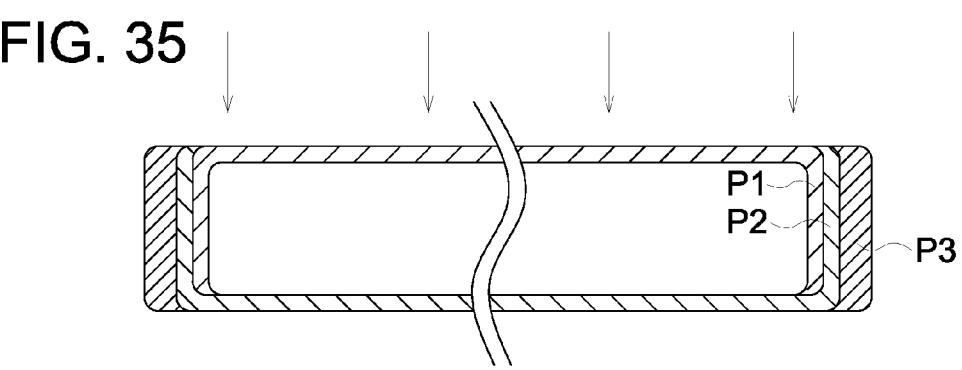
FIG. 35 is a sectional view showing a modified example of the housing body.

If third prepreg P3 having a predetermined thickness is arranged only at the side surfaces as it is shown in FIG. 35 to increase strength of the side surfaces of housing body 31, strength can be increased by increasing thickness of the side surfaces relating to strength such as twist and warp, while further keeping the amount of radiation penetrating the top surface, and thereby a permissible weight of the patient at a time of full load photographing can be increased.

Figure 36:
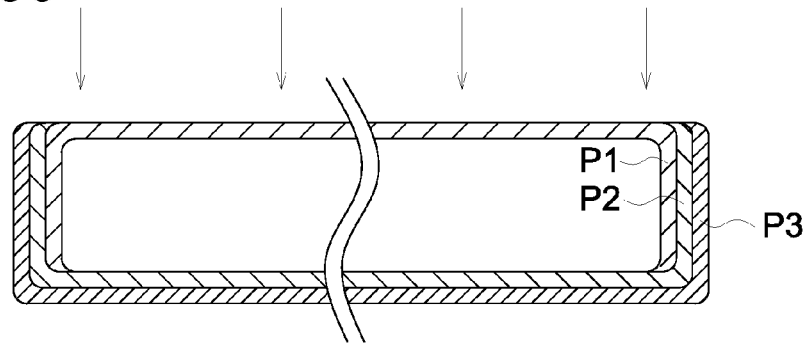
FIG. 36 is a sectional view showing a modified example of the housing body.

As it is shown in FIG. 36, by making only the top surface of housing body 31 with first prepreg P1 only, and by making the undersurface a double-layered structure and the side surfaces a three-layer structure, the undersurface and the side surfaces can be strengthened.

Figure 37A:
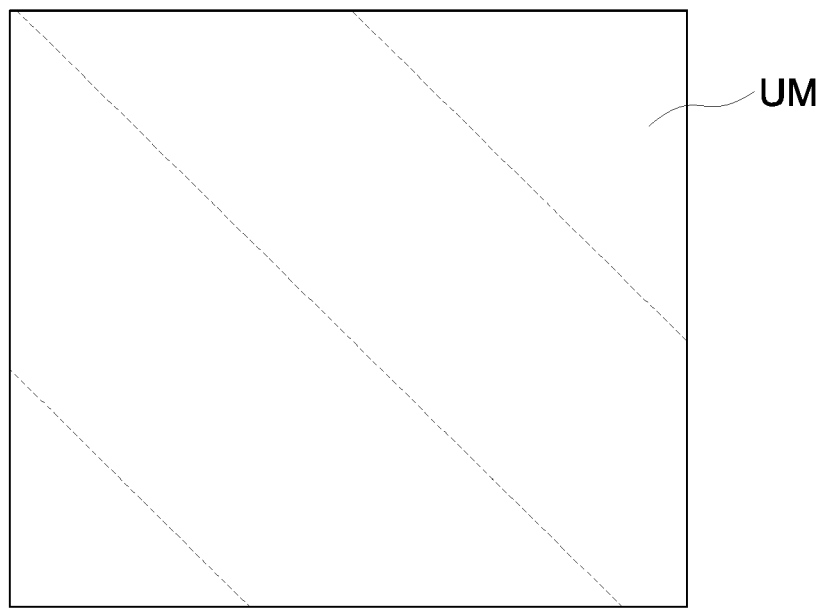
FIGS. 37a and 37b are a top view and a bottom view showing a modified example of the housing body.
Figure 37B:
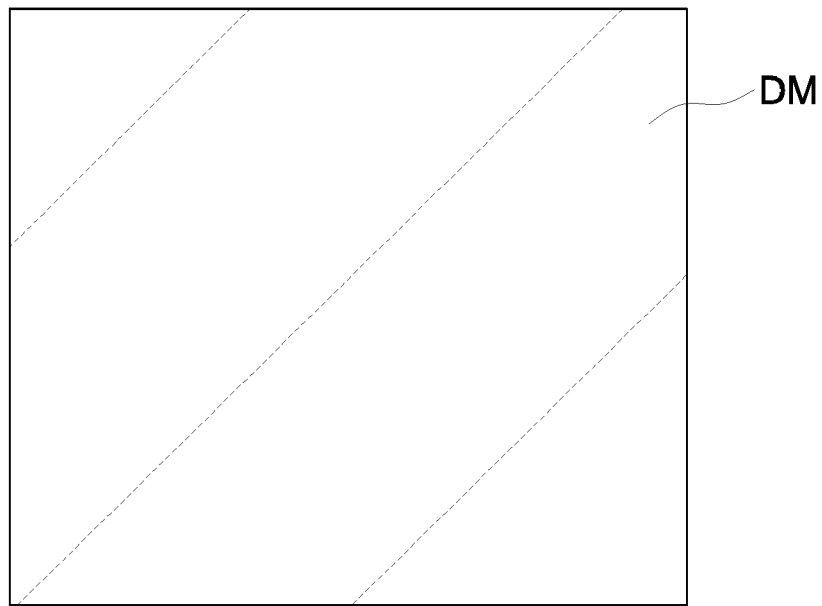

FIGS. 37*a* and 37*b* show a modified example showing top surface UM and undersurface DM of housing body 31 (refer to FIG. 3). Broken lines show the folding direction of carbon fibers, and, in the modified examples of FIGS. 37*a* and 37*b*, the folding directions of carbon fibers on top surface UM and undersurface DM are made to intersect each other. In this way, the direction dependency of torsion rigidity can be relaxed.

In the present embodiment, the FPD of indirect conversion method which is configured with scintillator layer 211 and signal detection section 151 was described as an example, but the FPD is not limited to the one of the indirect conversion method. For example, even in the FPD of direct conversion method in which amorphous serene (a-Se) layer, which absorbs radiation to covert the radiation into charge, is arranged, and which method directly converts (converting into electric signals) radiation energy of radiation irradiated onto a detector by bringing radiation photons into the above a-Se layer with a high voltage into the amount of charges, the configuration of the present invention, in which a-Se layer is sandwiched between two glass substrates, can be applied.

In the present embodiment, an example was a case in which scintillator layer 211 is a phosphor layer in which phosphor was allowed to vapor-grow on a support, and, by pasting above scintillator layer 211 on one surface of first glass substrate 214, scintillator layer 211 is formed on glass substrate 214. But scintillator layer 211 is not limited to the above case, and, for example, the scintillator layer may be formed on first glass substrate by a method such that the phosphor is directly vapor-deposited on the undersurface of the first glass substrate (the side opposite to incident radiation).

Further, the present embodiment has a configuration that signal detection section 151 is formed on second glass substrate 213, but the configuration may be such that signal detection section 151 is formed separately from second glass substrate, which is then placed on the second glass substrate.

In the present embodiment, there was described a case in which the glass surface was scratched using a laser as a smoothing method to smooth an end surface, but the smoothing method is not limited to one exemplified here. For example, an end surface may be smoothed by ex-post treatment such that the first and second glass substrates are cut using cemented carbide, diamond or the like, after which the cut end surface is polished or the cut end surface is subjected to heat treatment using a laser.

In the present embodiment, there was described a case in which a two-step process that the glass surface is scratched by a laser, after which the glass is cut (divided), but a single step which carries out up to a cutting step of the glass substrate by a laser may be used.

In the present embodiment, there was described a case in which, as a power supply section, a rechargeable secondary battery (rechargeable battery 25) is used, but the power supply section is not limited to the secondary battery. For example, a primary battery, which needs a battery replacement, such as a manganese cell, a nickel-cadmium cell, a mercury cell, and a lead cell may be used.

Other than the above, the present invention is not limited to the above embodiment, and it is obvious that appropriate changes may be made.

The cassette type radiographic image solid-state detector relating to the present embodiment, while keeping the amount of penetrating radiation, has sufficient strength, and it is possible to restrain deformation of a housing against stress from the outside, and therefore, the detector can cope with an impact from the outside, and it is possible to make a portable radiographing including radiographing at full load.

What is claimed is:

1. A cassette type radiographic image solid-state detector comprising:
    a detector unit including a scintillator for converting incident radiation into light and a detection section which receives and converts the light converted by the scintillator into electric signals; and
    a housing containing the detector unit, the housing including a rectangular tubular housing body formed of carbon fiber and having openings on both ends, and a first cover member and a second cover member for covering the openings of the rectangular tubular housing body,
    wherein a wall of the rectangular tubular housing body facing to a direction perpendicular to an incident direction of radiation is thicker than a wall of the rectangular tubular housing body facing to the incident direction of radiation.

2. The cassette type radiographic image solid-state detector described in claim 1,
    wherein the rectangular tubular housing body is formed by laminating members in each of which comprises fibers of carbon in which epoxy resin is impregnated.

3. The cassette type radiographic image solid-state detector described in claim 2,
    wherein a number of the laminated members of the wall facing to the direction perpendicular to the incident direction of radiation of the rectangular tubular housing body is larger than a number of the laminated members of the wall facing to the incident direction of radiation of the rectangular tubular housing body.

4. The cassette type radiographic image solid-state detector described in claim 2,
    wherein bundles of carbon fiber are weaved in an orthogonal direction in at least one of the laminated members

5. The cassette type radiographic image solid-state detector described in claim 2,
wherein a number of the laminated members of the wall of the rectangular tubular housing body facing to the incident direction of radiation is smaller than a number of the laminated members of a wall of an opposite side to the wall facing to the incident direction of radiation of the rectangular tubular housing body.

6. The cassette type radiographic image solid-state detector described in claim 2,
wherein the laminated members are prepregs.

7. The cassette type radiographic image solid-state detector described in claim 2,
wherein at least one of the laminated members of the wall facing to the direction perpendicular to the incident direction of radiation of the rectangular tubular housing body is thicker than each of the laminated members of the wall facing to the incident direction of radiation of the rectangular tubular housing body.

8. The cassette type radiographic image solid-state detector described in claim 1,
wherein the wall facing to the incident direction of radiation of the rectangular tubular housing body is thinner than a wall of an opposite side to the wall facing to the incident direction of radiation of the rectangular tubular housing body.

9. The cassette type radiographic image solid-state detector described in claim 1,
wherein the carbon fiber is pitch-based carbon fiber.

10. The cassette type radiographic image solid-state detector described in claim 1,
wherein a direction of the carbon fiber of the wall facing to the incident direction of radiation of the rectangular tubular housing body crosses a direction of the carbon fiber of a wall of an opposite side to the wall facing to the incident direction of radiation of the rectangular tubular housing body, by viewing in the incident direction.

* * * * *